US012592314B2

(12) United States Patent
Garber et al.

(10) Patent No.: US 12,592,314 B2
(45) Date of Patent: \*Mar. 31, 2026

(54) PATENT TREATMENT STATUS NOTIFICATION SYSTEM

(71) Applicant: Reliant MSO, LLC, Worcester, MA (US)

(72) Inventors: Lawrence D. Garber, Southborough, MA (US); Logan M. Garber, Southborough, MA (US); Sean M. McCarthy, Charlton, MA (US); Scott G. Pilate, Sturbridge, MA (US)

(73) Assignee: Reliant MSO, LLC, Worcester, MA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/467,357

(22) Filed: Sep. 14, 2023

(65) Prior Publication Data

US 2024/0006062 A1     Jan. 4, 2024

Related U.S. Application Data

(63) Continuation of application No. 15/946,218, filed on Apr. 5, 2018, now Pat. No. 11,810,664.

(Continued)

(51) Int. Cl.
*G16H 70/20*       (2018.01)
*G08B 5/36*        (2006.01)
(Continued)

(52) U.S. Cl.
CPC .............. *G16H 40/20* (2018.01); *G08B 5/36* (2013.01); *G08B 21/24* (2013.01); *G08B 25/08* (2013.01);
(Continued)

(58) Field of Classification Search
CPC .......... G08B 5/36; G08B 21/24; G08B 25/08; G08B 25/10; H05B 47/19; G06Q 10/1095
See application file for complete search history.

(56) References Cited

U.S. PATENT DOCUMENTS 3,810,096 A     5/1974   Kabat et al.
4,967,195 A    10/1990   Shipley
(Continued)

FOREIGN PATENT DOCUMENTS

JP          4647854 B2  \*  3/2011

OTHER PUBLICATIONS

Imperiali, M. et al. Networked Occupancy Sensor System. Mar. 2013. Worcester Polytechnic Institute. (Year: 2013).\*
(Continued)

*Primary Examiner* — Emily Huynh
(74) *Attorney, Agent, or Firm* — Alston & Bird LLP

(57) ABSTRACT

A system is described. The system includes a visual status indicator including a first light configured to indicate a first status and a second light configured to indicate a first identity. The system includes a control device for controlling the first and second lights, an electronic health record (EHR) controller configured to store data identifying a room occupant, and a central control circuit configured to cause the first light to change the first colored light to identify a second status based on an occurrence order of a plurality of statuses associated with a treatment cycle and one or more of receiving a first signal input by a user, receiving an occupancy detection signal, or receiving information from the EHR controller. The central control circuit is also configured to cause the second light to change the second colored light to identify a second identity selected from a plurality of identities.

18 Claims, 20 Drawing Sheets

Related U.S. Application Data

(60) Provisional application No. 62/503,735, filed on May 9, 2017.

(51) Int. Cl.

| | |
|---|---|
| *G08B 21/24* | (2006.01) |
| *G08B 25/08* | (2006.01) |
| *G08B 25/10* | (2006.01) |
| *G16H 10/60* | (2018.01) |
| *G16H 40/20* | (2018.01) |
| *G06Q 10/1093* | (2023.01) |
| *H05B 45/00* | (2022.01) |

(52) U.S. Cl.
CPC ............. *G08B 25/10* (2013.01); *G16H 10/60* (2018.01); *G06Q 10/1093* (2013.01); *H05B 45/00* (2020.01)

(56) References Cited

U.S. PATENT DOCUMENTS

| | | | | |
|---|---|---|---|---|
| 5,309,146 | A | * | 5/1994 | Kenet .................... G08B 13/19 |
| | | | | 340/567 |
| 5,760,704 | A | * | 6/1998 | Barton ................... G16H 40/20 |
| | | | | 340/286.07 |
| 7,994,900 | B1 | | 8/2011 | Langstroth et al. |
| 8,149,104 | B2 | | 4/2012 | Crum |
| 8,203,439 | B1 | | 6/2012 | Peters, Jr. et al. |
| 2002/0053969 | A1 | * | 5/2002 | Wagner .................... G08B 5/36 |
| | | | | 340/286.08 |
| 2007/0043822 | A1 | | 2/2007 | Brumfield |
| 2008/0014868 | A1 | * | 1/2008 | Davis ...................... H04L 12/66 |
| | | | | 455/41.2 |
| 2008/0033256 | A1 | * | 2/2008 | Farhan ................... G16H 40/63 |
| | | | | 600/300 |
| 2009/0066486 | A1 | * | 3/2009 | Kiekbusch ............. G08B 5/221 |
| | | | | 340/815.45 |
| 2009/0106051 | A1 | * | 4/2009 | Albro ..................... G06Q 10/06 |
| | | | | 705/3 |
| 2009/0138291 | A1 | | 5/2009 | Heinze |
| 2010/0088119 | A1 | * | 4/2010 | Tipirneni .............. G16H 80/00 |
| | | | | 705/3 |
| 2012/0044067 | A2 | * | 2/2012 | Crum ...................... G08B 5/36 |
| | | | | 340/521 |
| 2012/0126978 | A1 | | 5/2012 | Kellen et al. |
| 2016/0328952 | A1 | | 11/2016 | Will et al. |
| 2017/0061763 | A1 | | 3/2017 | Hanson et al. |
| 2018/0330813 | A1 | | 11/2018 | Garber et al. |

OTHER PUBLICATIONS

Global Dossier translation of written description of JP-4647854-B2. (Year: 2011).*

Imperiali, M. et al. Networ ed Occupancy Sensor System. Mar. 2013. Worcester Polytechnic Institute. (Year: 2013).

* cited by examiner

EXAMPLE OF 6 ROOM STATUSES

PATIENT TREATMENT STATUS NOTIFICATION SYSTEM

RELATED APPLICATIONS

This application is a continuation of U.S. application Ser. No. 15/946,218 filed Apr. 5, 2018, which claims priority to U.S. Provisional Patent Application No. 62/503,735 filed May 9, 2017, the contents of which are incorporated herein by reference in their entirety.

FIELD OF THE INVENTION

The disclosed subject matter herein relates generally to the healthcare industry and, more particularly, to patient treatment status notification systems and methods in healthcare facilities.

BACKGROUND

In the medical field, patients are commonly examined and treated by medical professionals at designated healthcare facilities, such as hospitals, medical groups and integrated healthcare organizations. To accommodate an ever-increasing volume of patients, often on a daily basis, medical treatment facilities are typically designed with a large quantity of individual examination rooms.

To maximize operational efficiency while preserving effective healthcare, patient treatment is typically rendered by a team of various healthcare professionals, including physicians, nurses, medical assistants and office administrators. By delegating certain responsibilities amongst a broader team of individuals, a highly skilled professional (e.g., a physician) is able to tend to a larger number of patients in a more time-efficient manner.

For instance, the following represents a common chain of medical interaction with a patient. After being checked-in by an office administrator, the patient is assigned to a particular examination room. Thereafter, a medical assistant commonly engages in some preliminary examination steps, such as measuring vital signs and speaking with the patient to gather pertinent medical information. Once completed, a physician then performs a detailed medical examination of the patient. Based on the examination, the physician may then instruct a nurse or medical assistant to undertake a certain course of action, such as administer a vaccine or draw blood for testing. The chain of treatment continues, as needed, amongst the various professionals within the healthcare team until the patient treatment process is complete. Once finished, the patient exits the examination room, thereby rendering it available for cleaning and then use by the next patient in need of treatment.

Patient information is commonly shared amongst the various members of the healthcare team through the use of notes created using electronic health records system software. For instance, requested medical orders are often accessed using any linked computer or electronically delivered to specified personnel (e.g., via a designated mobile device or smart watch).

Although commonplace in the industry, it has been found that healthcare facilities that rely upon a chain of medical treatment administered by a team of various professionals often experience a notable impediment. Specifically, it has been found that certain professionals amongst the healthcare team are not always readily aware of the exact moment when his/her services are required for an ordered task in a particular examination room.

Healthcare organizations are also striving to improve the flow of patients through a limited number of exam rooms by allowing multiple physicians to share exam rooms. In the past, physicians had their own dedicated exam rooms which, with team-based care, could mean that one physician's rooms are all occupied and have more patients waiting, even though another physician may have an empty room. The shift to sharing non-dedicated rooms allows for optimal use of a limited number of exam rooms, but creates an issue of knowing which exam rooms contain a particular physician's patients, and which patient should the physician see next.

To facilitate the passing of responsibility amongst the various professionals that constitute a particular healthcare team and identifying which rooms contain a particular physician's patients, medical treatment facilitates often utilize a flag system to notify the team of the particular stage of patient treatment within each examination room. Using the flag system, a flag of a first color may be used to denote that the patient is awaiting examination by a physician, a flag of a second color may be used to denote that the patient is in the process of being examined by a physician, and a flag of third color may be used to denote that the physician has completed examination of the patient. Other flags or combinations of flags could be used to denote which physician's patient is in a given room and perhaps where the physician should go next. In this manner, albeit somewhat complex, other members of the healthcare team can discern when assistance may be required and/or the impending availability of a certain examination room.

Although well-known and widely used in the art, flag systems of the type as described above have been found to be limited in not only scalability, due to the limited number of available flags, but also overall efficiency. In particular, the manual task of remembering the color code designation for each of the various notification flags and, in turn, changing the sequence of flags in the proper location throughout the patient examination process has been found to be largely cumbersome and, as such, is not always properly utilized.

In addition to physical flag systems of the type as described above, light signaling systems have grown in prominence in medical facilities to notify a healthcare team of, among other things, which examination rooms are occupied, where patients and staff members are located, and which patients require attention. An example of such a light signaling system notification system is currently available for sale by Expeditor Systems, Inc. However, such light signaling systems typically provide only a limited amount of information and are relatively cumbersome to operate.

Accordingly, in view of the above, it is an object of the disclosed subject matter to provide a healthcare facility that is so equipped, with a novel, scalable, user-intuitive and easily administrable system for notifying a healthcare team of the treatment status of the patients located within each active examination room.

SUMMARY

In one aspect, the disclosed subject matter discloses a patient treatment status notification system in a healthcare facility with multiple examination rooms, which includes a first electronic visual status indicator and a second electronic visual status indicator to be installed outside a first examination room, an indicator control circuit configured to communicate with and control the first and second electronic visual status indicators of the first examination room, a manual input device for the first examination room configured to receive user input representing change of a treatment status of a patient assigned to the first examination room, a switch multiplexer configured to communicate with and receive the user input from the manual input device for the first examination room, and a central control processor coupled to the indicator control circuit and the switch multiplexer to update the treatment status of the first examination room.

In some embodiments, each of the first and second electronic visual status indicators of the first examination room comprises a multicolor light emitting diode (LED).

In some embodiments, the first electronic visual status indicator of the first examination room is configured to emit color light to represent the treatment status of the patient assigned to the first examination room, and the second electronic visual status indicator of the first examination room is configured to emit color light to identify a primary healthcare provider for the patient assigned to the first examination room.

In some embodiments, the first electronic visual status indicator of the first examination room is configured to emit color light to represent the status of the examination room when not occupied by a patient.

In some embodiments, the patient treatment status notification system also includes an occupancy sensor in the first examination room configure to detect occupancy in the first examination room, wherein the switch multiplexer is configured to communicate with and receive occupancy detection signal from the occupancy sensor in the first examination room and the central control processor is configured to update the treatment status of the first examination room at least based on the occupancy detection signal from the first examination room.

In some embodiments, the patient treatment status notification system also includes a door sensor for the first examination room configured to detect opening and closing of a door of the first examination room, wherein the switch multiplexer is configured to communicate with and receive door detection signal from the door sensor for the first examination room and the central control processor is configured to update the treatment status of the first examination room at least based on the door detection signal from the first examination room.

In some embodiments, the patient treatment status notification system also includes an electronic health record (EHR) controller coupled with a computing device in the first examination room and configured to communicate with an EHR system.

In some embodiments, the second electronic visual status indicator of the first examination room is configured to emit light of a color to identify a primary healthcare provider for the patient assigned to the first examination room, based on access of a medical record of the patient associated with the primary healthcare provider in the EHR system via the computing device in the first examination room.

In some embodiments, the first electronic visual status indicator of the first examination room is configured to emit light of a color to identify the treatment status of the patient assigned to the first examination room and/or the status of the examination room when not occupied by a patient, based on a healthcare team member's entry into the EHR system or the primary healthcare provider's access to the EHR system via the computing device in the first examination room.

In some embodiments, the EHR controller is further configured to communicate treatment data regarding the patient of the first examination room to the EHR system, the data including at least one of treatment start time, treatment duration, patient wait time, and delay of the patient.

In some embodiments, the central control processor is configured to trigger a push notification by the EHR system via the EHR controller to notify a healthcare team member who is next to treat the patient assigned to the first examination room, the push notification including information about the patient and the first examination room.

In some embodiments, the first electronic visual status indicator of the first examination room is configured to emit light of a color to identify the treatment status of the patient assigned to the first examination room, based on access of a medical record of the patient in the EHR system.

In some embodiments, the first electronic visual status indicator of the first examination room is configured to blink at a first rate to indicate if the patient in the first examination room is currently waiting.

In some embodiments, a first electronic visual status indicator for a second examination room where a patient therein has waited the longest time among all current patients for a given primary healthcare provider is configured to blink at a second rate, wherein the second rate is higher than the first rate.

In some embodiments, the first electronic visual status indicator for the first examination room is further configured to blink at the first rate after a period of time to indicate that the patient needs to be re-examined.

In some embodiments, a first electronic visual status indicator for a first examination room is configured for a particular status to stop blinking when the manual input device receives a user input or is invoked by a healthcare team member's entry into the EHR system via a computing device. These actions reset the starting time after which a configured period of time can elapse to indicate that the patient needs to be re-examined.

In some embodiments, a first electronic visual status indicator for a first examination room where a patient therein has waited longer than a configured period of time in that status, is configured to blink at a second rate, wherein the second rate is higher than the first rate.

In some embodiments, a manual input device for a second examination room where a patient therein has waited the longest time among all current patients for a given primary healthcare provider, configured to receive user input representing change of a treatment status reassigning that patient to be seen last among all current patients for a given primary healthcare provider, wherein the first electronic visual status indicator for this second examination room changes to blink from a second rate to a first rate, while the first electronic visual status indicator for the examination room where a patient therein has waited the second longest time among all current patients for a given primary healthcare provider changes to blink from a first rate to a second rate, wherein the second rate is higher than the first rate.

In some embodiments, the manual input device for the first examination room comprises a rotary pushbutton that receives a press action and at least one of a clockwise rotation action and a counterclockwise rotation action from a user.

In some embodiments, the manual input device for the first examination room can be depressed once, twice in rapid succession, or three times in rapid succession in order to advance the room status one step, two steps, or three steps, respectively.

In some embodiments, the manual input device for the first examination room can be rotated clockwise to advance the room status forward one or more steps, or rotated counter-clockwise to revert the room status one or more steps.

In some embodiments, the first electronic visual status indicator in the first examination room is configured to emit light of a different color to represent a different treatment status when the manual input device receives a user input.

In some embodiments, the first electronic visual status indicator in the first examination room is configured to emit light of a different color to represent a different treatment status based on a healthcare team member's entry into the EHR system.

In some embodiments, the first electronic visual status indicator in the first examination room is configured to emit light alternating between two or more different colors to represent a different treatment status when the manual input device receives a user input or based on a healthcare team member's entry into the EHR system.

In some embodiments, the patient treatment status notification system also includes a medical emergency input device in the first examination room, when activated by a user, configured to generate a medical emergency signal.

In some embodiments, the medical emergency signal of the first examination room is displayed by at least one of the first and second electronic visual status indicators for the first examination room.

In some embodiments, the medical emergency signal of the first examination room is displayed by at least one of a first and a second electronic visual status indicators for a second examination room.

In some embodiments, the medical emergency signal displayed by at least one of a first and a second electronic visual status indicators for at least two second examination rooms are displayed sequentially in a pattern that leads responders to a first examination room.

In some embodiments, the patient treatment status notification system also includes a communication interface coupled to a public emergency response system, wherein the medical emergency signal is sent to the public emergency response system via the communication interface dependent upon at least one of time and day of the medical emergency signal.

In some embodiments, the patient treatment status notification system also includes a communication interface coupled to a facility speaker system, wherein an audible medical emergency signal or message is sent to the facility speaker system via the communication interface dependent upon at least one of time and day of the medical emergency signal.

In some embodiments, the patient treatment status notification system also includes a central display system configured to display the treatment status of the first examination room and the identity of the primary healthcare provider of the patient assigned to the first examination room.

In some embodiments, the patient treatment status notification system also includes a central display system configured to display the treatment status of the first examination room and the identity of the primary healthcare provider of the patient assigned to the first examination room along with data including at least one of treatment start time, treatment duration, patient wait time, and delay of the patient.

In some embodiments, the patient treatment status notification system also includes a plurality of configurable examination room statuses, each of which is functionally linked to each other representing workflow steps.

In some embodiments, the patient treatment status notification system also includes a plurality of configurable examination room statuses, each of which is sequentially linked such that the workflow typically advances forward from one status to the configurable but consistently-linked subsequent status, and when reverting backwards through the workflow, a status moves to a configurable but consistently-linked prior status.

In some embodiments, the patient treatment status notification system also includes a plurality of configurable examination room statuses, each of which is sequentially linked in a cycle such that when advancing forward through statuses, the last status is followed by the first status, and when reverting backwards through statuses, the first status is followed by the last status.

In another aspect, the disclosed subject matter discloses a patient treatment status notification system in a healthcare facility with multiple examination rooms, which includes a first electronic visual status indicator and a second electronic visual status indicator to be installed outside an examination room, wherein the first electronic visual status indicator is configured to emit color light to represent the treatment status of a patient assigned to the examination room and the second electronic visual status indicator is configured to emit color light to identify a primary healthcare provider for the patient assigned to the examination room, an indicator control circuit configured to communicate with and control the first and second electronic visual status indicators of the examination room, a manual input device for the examination room configured to receive user input representing change of a treatment status of a patient assigned to the examination room, wherein the manual input device is configured to receive a press action and at least one of a clockwise rotation action and a counterclockwise rotation action from a user, a switch multiplexer configured to communicate with and receive the user input from the manual input device for the examination room, an electronic health record (EHR) controller coupled with a computing device in the examination room and configured to communicate with an EHR system, and a central control processor coupled to the indicator control circuit, the switch multiplexer, and the EHR controller to update the treatment status of the examination room.

In some embodiments, the patient treatment status notification system also includes an occupancy sensor in the examination room configured to detect occupancy in the first examination room, a door sensor for the examination room configured to detect opening and closing of a door of the examination room, a medical emergency input device in the examination room, when activated by a user, configured to generate a medical emergency signal, a communication interface coupled to a public emergency response system, wherein the medical emergency signal is sent to an emergency response system via the communication interface dependent upon at least one of time and day of the medical emergency signal, a communication interface coupled to a facility speaker system, wherein an audible medical emergency signal or message is sent to the facility speaker system via the communication interface dependent upon at least one of time and day of the medical emergency signal, and a central display system configured to display the treatment status of the examination rooms and the identity of the primary healthcare provider of the patient assigned to each examination room along with data including at least one of treatment start time, treatment duration, patient wait time, and delay of the patient.

In yet another aspect, the disclosed subject matter discloses a method of displaying patient treatment status notifications in a healthcare facility with multiple rooms, which includes activating a first electronic visual status indicator installed outside an examination room to emit color light to represent a treatment status of a patient assigned to the examination room, activating a second electronic visual status indicator installed outside the examination room to emit color light to identify a primary healthcare provider for the patient assigned to the examination room, controlling the first and second electronic visual status indicators of the examination room by an indicator control circuit, receiving user input representing change of the treatment status of the patient via a manual input device, wherein the user input is one of a press action, a clockwise rotation action, and a counterclockwise rotation action, receiving the user input from the manual input device for the examination room by a switch multiplexer, communicating with an electronic health record (EHR) system via an EHR controller, which is coupled with a computing device in the examination room, and updating the treatment status of the examination room based on the user input and information received from the EHR system.

In some embodiments, the method of displaying patient treatment status notifications also includes receiving user input representing change of the treatment status of the patient via a manual input device, wherein the user input is one of a single-press action, a double-press action, a triple-press action, a clockwise rotation action, and a counterclockwise rotation action, receiving user input representing a medical emergency for the patient via a medical emergency input device, wherein the user input is a press action, receiving input representing change in occupancy status for the examination room via an occupancy sensor and/or door sensor, receiving the user input from the manual input device, the medical emergency input device, the occupancy sensor and the door sensor for the examination room by a switch multiplexer, announcing a medical emergency status of the examination room via a facility speaker system, communicating a medical emergency status of the examination room via an emergency response system, and displaying the treatment status of the examination room on a central display system.

BRIEF DESCRIPTION OF THE DRAWINGS

In the drawings, wherein like reference numerals represent like parts.

DETAILED DESCRIPTION

I. Healthcare Facility 11

Figure 1:
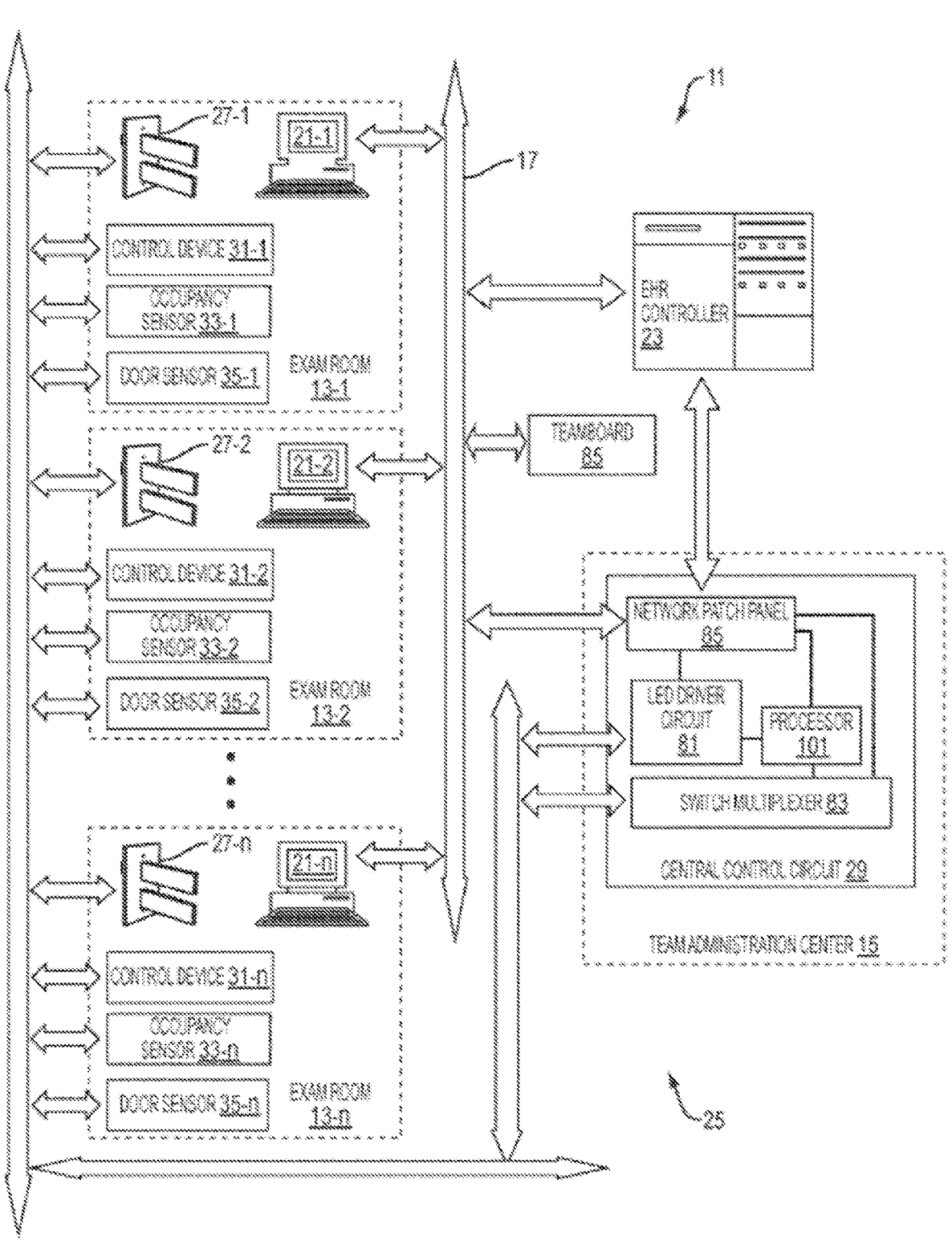
FIG. 1 contains a schematic representation of a patient treatment status notification system in a healthcare facility, according to certain embodiments of the disclosed subject matter herein.

FIG. 1 contains a schematic representation of a patient treatment status notification system (eFLAG system) 25 in a healthcare facility 11, according to certain embodiments of the disclosed subject matter herein. As explained in detail below, the healthcare facility 11 is equipped with an enhanced means for tracking and displaying patient treatment status in real time.

As defined herein, the healthcare facility 11 can represent any medical environment where patients are routinely examined and treated by a team of healthcare professionals. For instance, the healthcare facility 11 may represent, inter alia, a hospital, medical group or integrated healthcare organization.

The healthcare facility 11 can include a set of examination or treatment rooms 13-1 thru 13-$n$ that can be managed by personnel organized through a team administration center or station 15, located in close proximity thereto. Together, rooms 13-1 through 13-$n$ and administration center 15 can form a designated unit or department, within the larger healthcare facility 11. For ease of illustration and understanding, the healthcare facility 11 is represented schematically as comprising a single unit. However, it is to be understood that the healthcare facility 11 can include a plurality of distinct units to accommodate various healthcare team practices.

Additionally, in the description that follows, the electronic architecture of the disclosed subject matter herein can be designed to provide electronic patient treatment status notifications for a unit consisting multiple (e.g., 8-12) examination rooms. However, it should be noted that the electronic architecture of the disclosure subject matter herein is readily scalable and, as such, can be modified to accommodate a greater number of examination rooms 13 within each unit.

The healthcare facility 11 can be equipped with a computer network 17 for compiling and communicating electronic health records. Specifically, the healthcare facility 11 can include a plurality of computing devices 21-1 thru 21-$n$, each of which can be located within a corresponding examination room 13 inside the healthcare facility 11. Each computing device 21, in turn, can be electronically linked with an electronic health record (EHR) controller 23 that receives, organizes, and stores patient data compiled from each individual computing device 21 in each unit of the healthcare facility 11. In this manner, the EHR controller 23 can serve as a hub of computer network 17.

In some embodiments, the EHR controller 23 is represented as a single network server that is programmed with appropriate electronic health records software. For instance, the computer network 17 may rely upon electronic health records software of the type which is rendered available in the marketplace by Epic Systems Corporation.

In some embodiments, the EHR controller 23 is represented as being located within the healthcare facility 11. However, it should be noted that the EHR controller 23 need not be located within the healthcare facility 11. Rather, it is to be understood that the EHR controller 23 can be remotely located and operate as the hub of a secure, cloud-based, health records system.

In operation, the computing devices 21 can be accessed by healthcare professionals assigned to treat patients within each unit of the healthcare facility 11. As explained below, the EHR controller 23 is able to readily identify the particular examination room 13 in which each computing device 21 is located (e.g., through the use of a cross-reference table).

II. Patient Treatment Status Notification System (eFLAG System) 25

As explained in detail below, the healthcare facility 11 is equipped with an electronic notification system (eFLAG system) 25 for communicating the treatment status of the patient located within each examination room 13. Via electronic patient treatment status notifications, the eFLAG system 25 can facilitate the transition of patient care responsibilities amongst the team of healthcare professionals responsible for a particular unit. In some embodiments, the eFLAG system 25 can be integrated or linked with the computer network 17 and the EHR controller 23.

In some embodiments, the eFLAG system 25 can comprise a plurality of visual status indicators 27-1 thru 27-$n$, with one visual status indicator 27 designated and installed in the immediate vicinity of each examination room 13. Each visual status indicator 27 can be electronically linked with a central control circuit 29 that can be located at the team administration center 15, as will be explained further in detail below.

Each visual status indicator 27 can provide a user intuitive way for determining the real-time examination status of a patient assigned to a particular examination room 13. In some embodiments, a visual status indicator 27 can indicate the examination status of a patient through a configurable cycle of color-coded lights. In this manner, patients can be treated by the healthcare team in an efficient, timely, and effective fashion.

In some embodiments, the eFLAG system 25 can include a plurality of control devices 31-1 thru 31-$n$, with one control device 31 installed in the immediate vicinity of each examination room 13. Each control device 31 can be electronically linked with the central control circuit 29, as will be explained further in detail below. The illumination status of each visual status indicator 27 can be updated through manual actuation of its corresponding control device 31 (i.e., the control device 31 designated for the same examination room 13).

In some embodiments, the eFLAG system 25 can also comprise a plurality of occupancy sensors 33-1 thru 33-$n$ as well as a plurality door sensors 35-1 thru 35-$n$, with one occupancy sensor 33 and one door sensor 35 installed in each examination room 13 in electronic communication with the central control circuit 29. For example, each occupancy sensor 33 can detect occupancy in the examination room 13 (e.g., by motion, heat, etc.) and may be in the form of a low voltage ceiling sensor of the type manufactured and sold by Cooper Controls under its OAC-DT line of sensors. For another example, each magnetic door sensor 35 may be in the form of a magnetic door sensor manufactured by UXCell of Hong Kong. Together, each complementary set of sensors 33 and 35 can allow for automatic update of its corresponding visual status indicator 27, thereby simplifying the overall operation of the eFLAG system 25. For instance, occupancy sensors 33 may be used in the configuration of the eFLAG system 25 to detect when a patient has exited an examination room (e.g., after changing into clothes and departing).

In some embodiments, the integration of the eFLAG system 25 with an electronic health records computer network, whether new or preexisting, can improve overall ease of operation. For example, the input of patient data by a medical assistant using a computing device 21 located in a particular room 13 can be used, inter alia, to automatically identify the examination room a patient is located and the particular physician that should be designated to administer the examination (e.g., based on a preexisting relationship or notable medical issue flagged in the patient health records). Similarly, communication between the eFLAG system 25 and the computer network 17 can help ensure that the proper patient status is displayed (e.g., resolving certain situations when one member of the healthcare team fails to properly activate the control device 31 to denote a change in patient treatment status).

III. Visual Status Indicator 27

Figure 2:
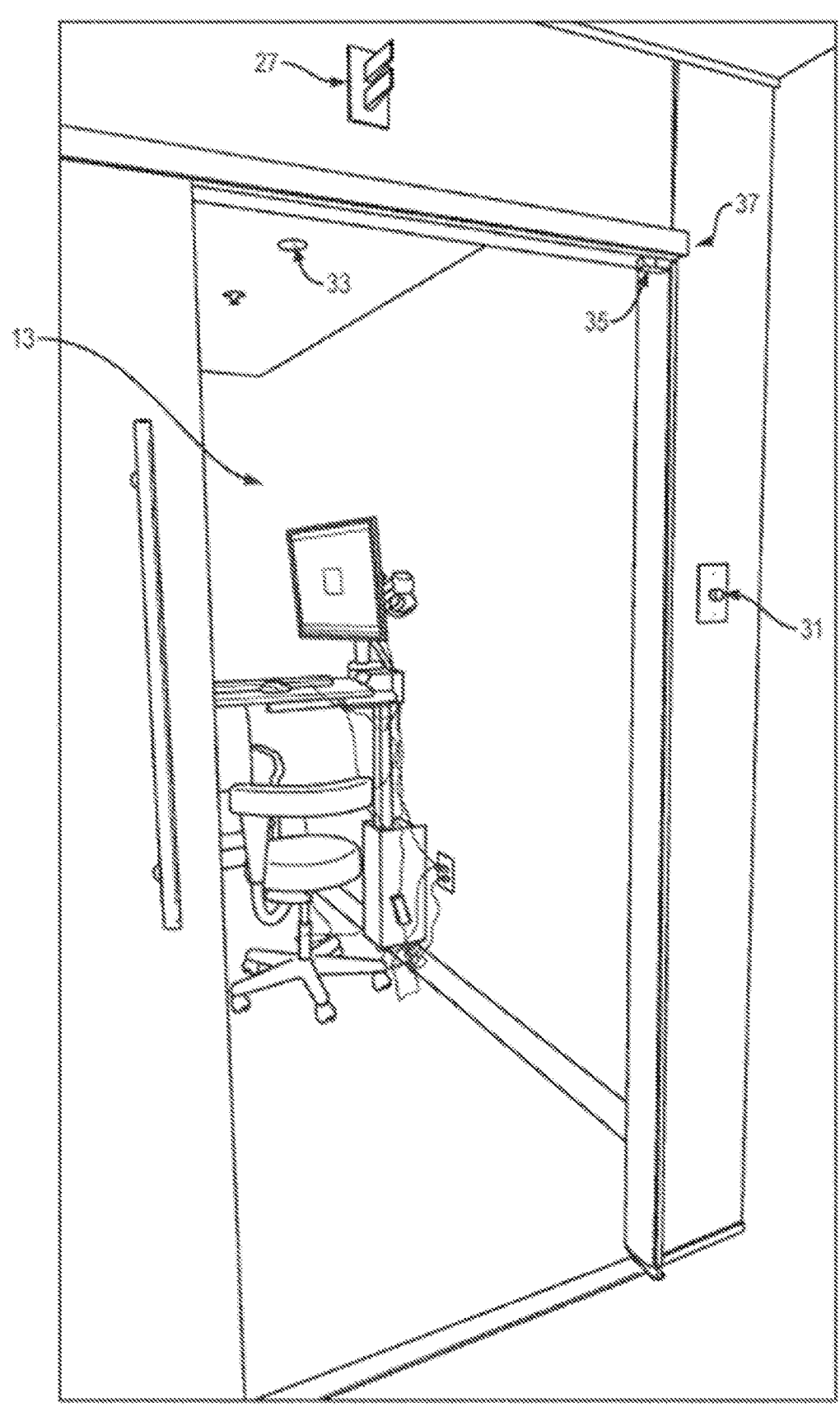
FIG. 2 shows a front perspective view of the immediate exterior region of one of the examination rooms illustrated in FIG. 1, according to certain embodiments of the disclosed subject matter herein.

Referring now to FIG. 2, each visual status indicator 27 can be installed outside its corresponding examination room 13 in a highly visible location. For instance, as illustrated in FIG. 2, the visual status indicator 27 is mounted along the top, outside portion of door frame 37 of the examination room 13 to ensure adequate visibility.

Figure 3A:
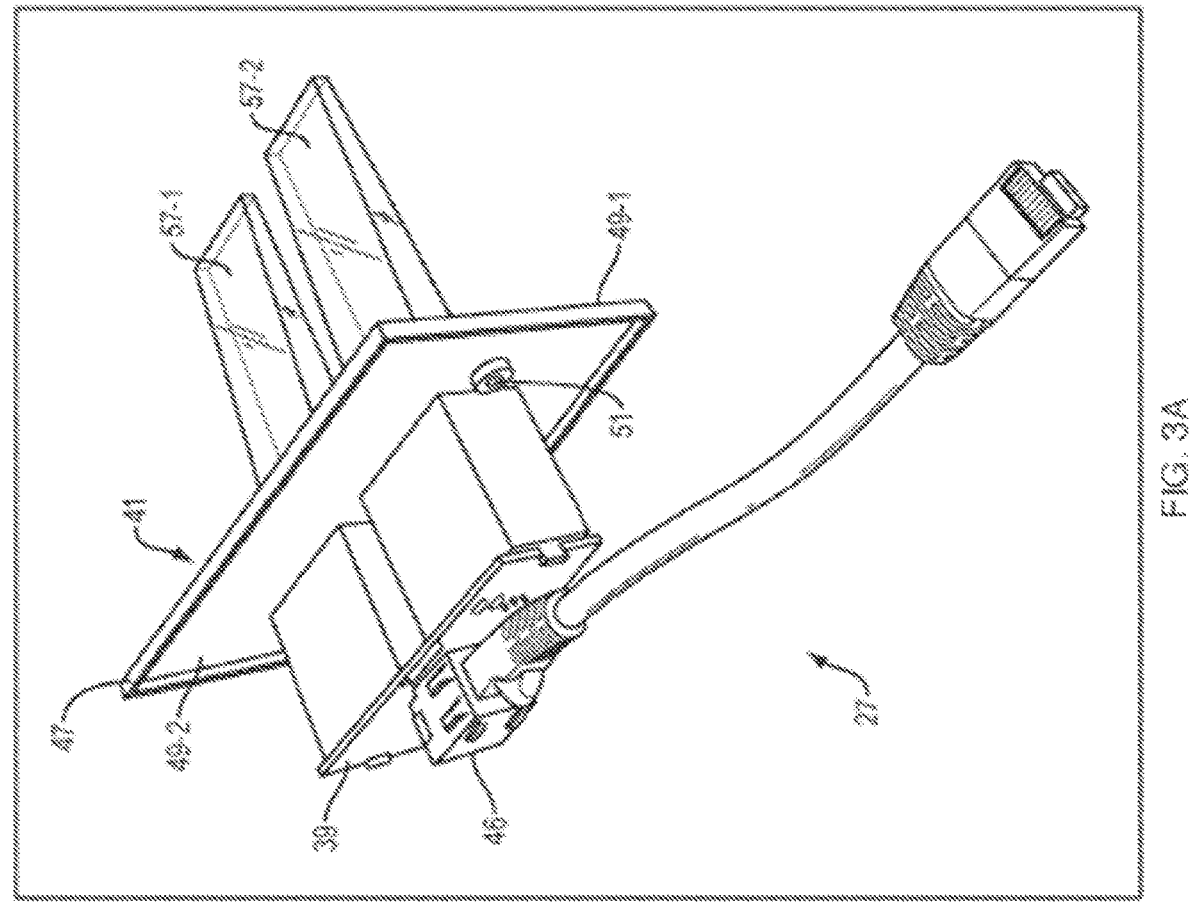
FIG. 3(a) shows a rear perspective view of the visual indicator illustrated in FIG. 2, wherein the visual indicator is shown with a network cable connected thereto, according to certain embodiments of the disclosed subject matter herein.
Figure 3B:
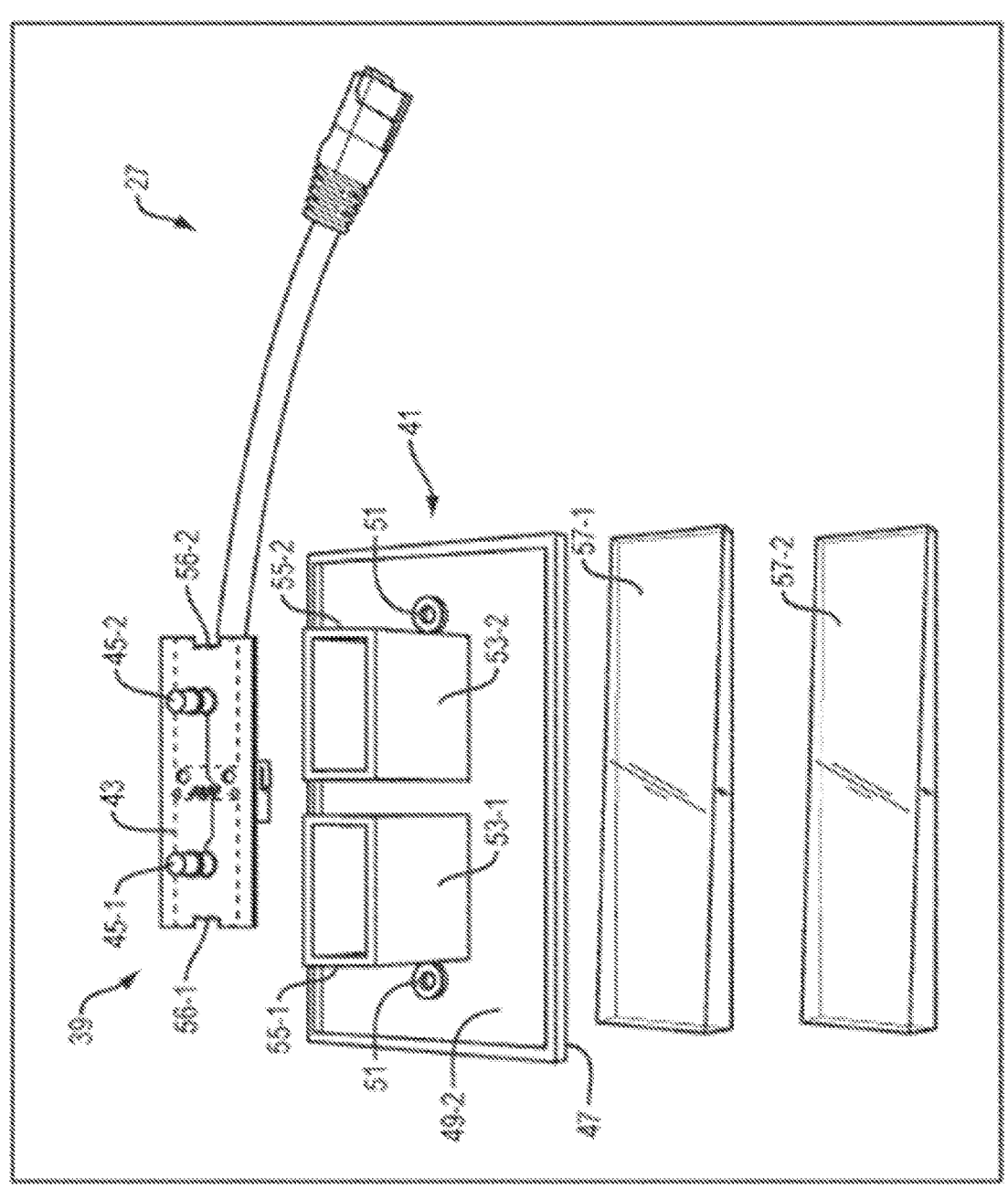
FIG. 3(b) shows an exploded view of the visual indicator illustrated in FIG. 2, wherein the visual indicator is shown with a network cable connected thereto, according to certain embodiments of the disclosed subject matter herein.
Figure 5:
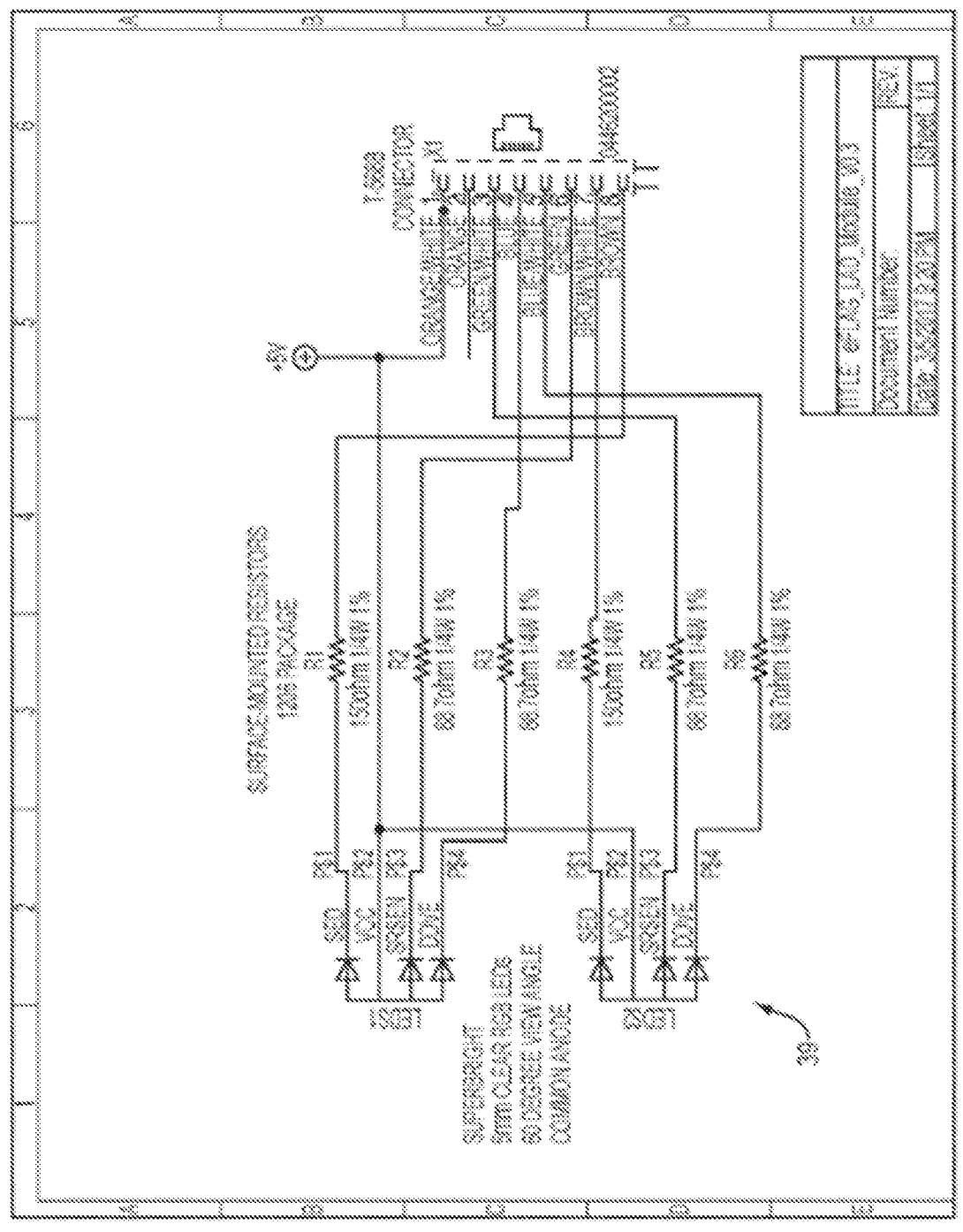
FIG. 5 shows an electrical schematic representation of the visual indicator illustrated in FIGS. 3(a) and 3(b), according to certain embodiments of the disclosed subject matter herein.
Figure 6:
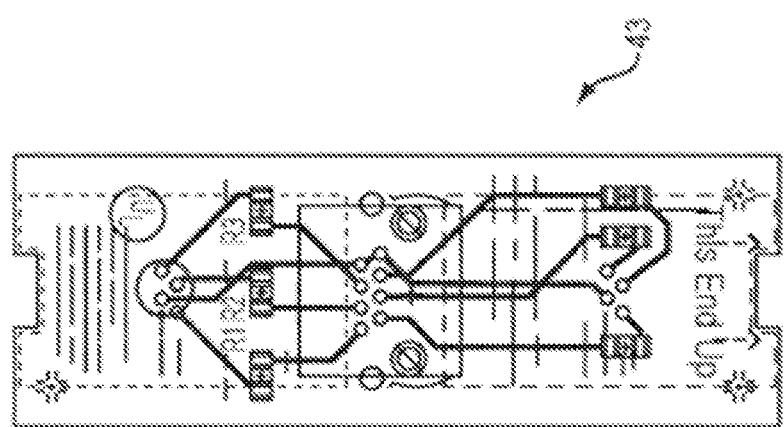
FIG. 6 shows a bottom plan view of the printed circuit board for the visual indicator illustrated in FIG. 3(b), according to certain embodiments of the disclosed subject matter herein.
Figure 7A:
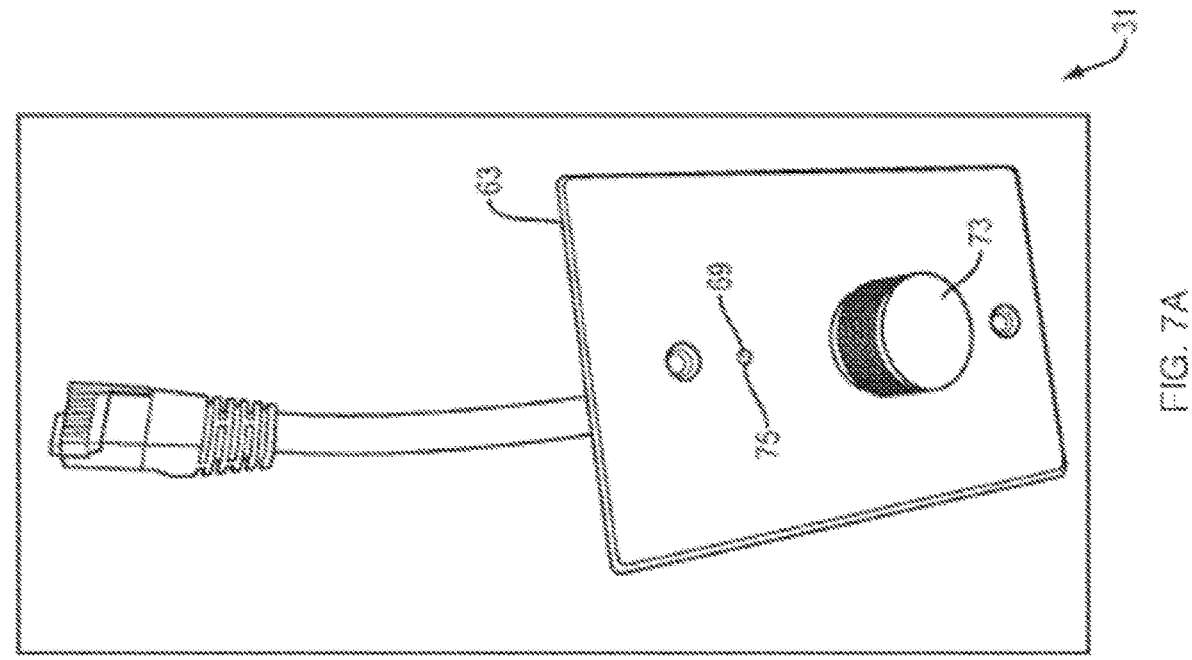
FIG. 7(a) shows a front perspective view of the control device illustrated in FIG. 2, wherein the control device is shown with a network cable connected thereto, according to certain embodiments of the disclosed subject matter herein.
Figure 7B:
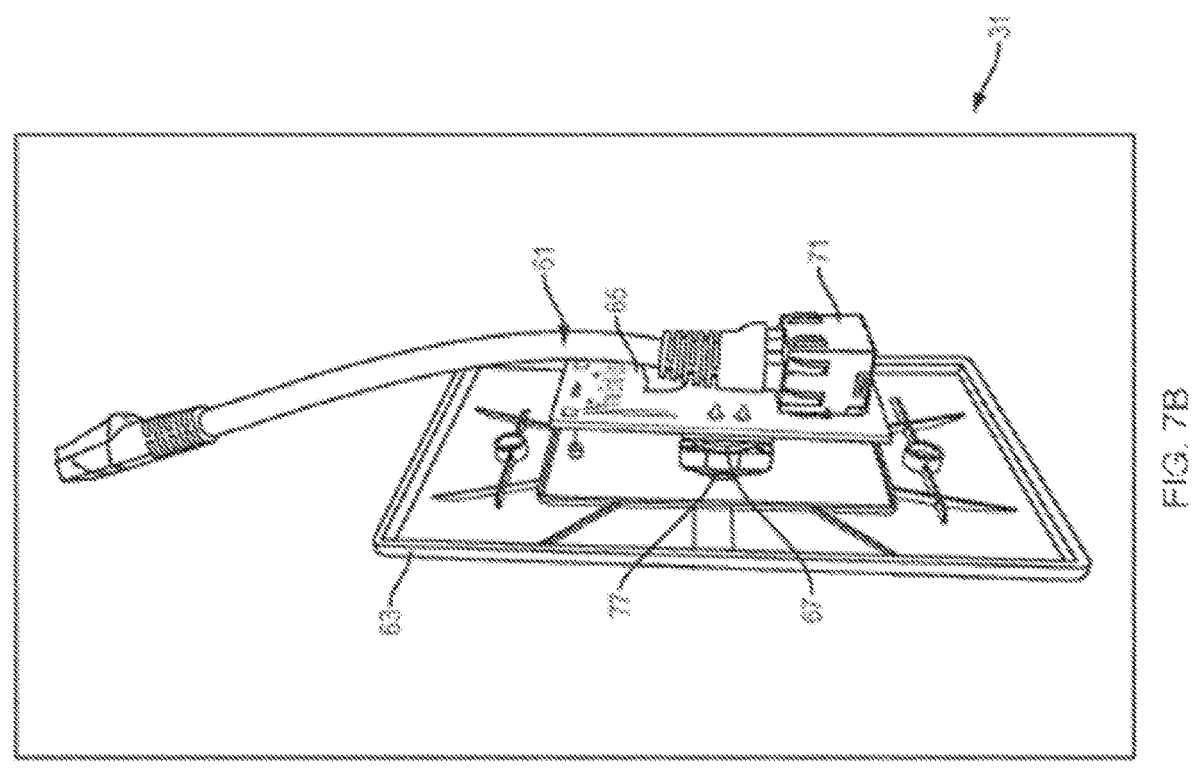
FIG. 7(b) shows a rear perspective view of the control device illustrated in FIG. 2, wherein the control device is shown with a network cable connected thereto, according to certain embodiments of the disclosed subject matter herein.
Figure 8:
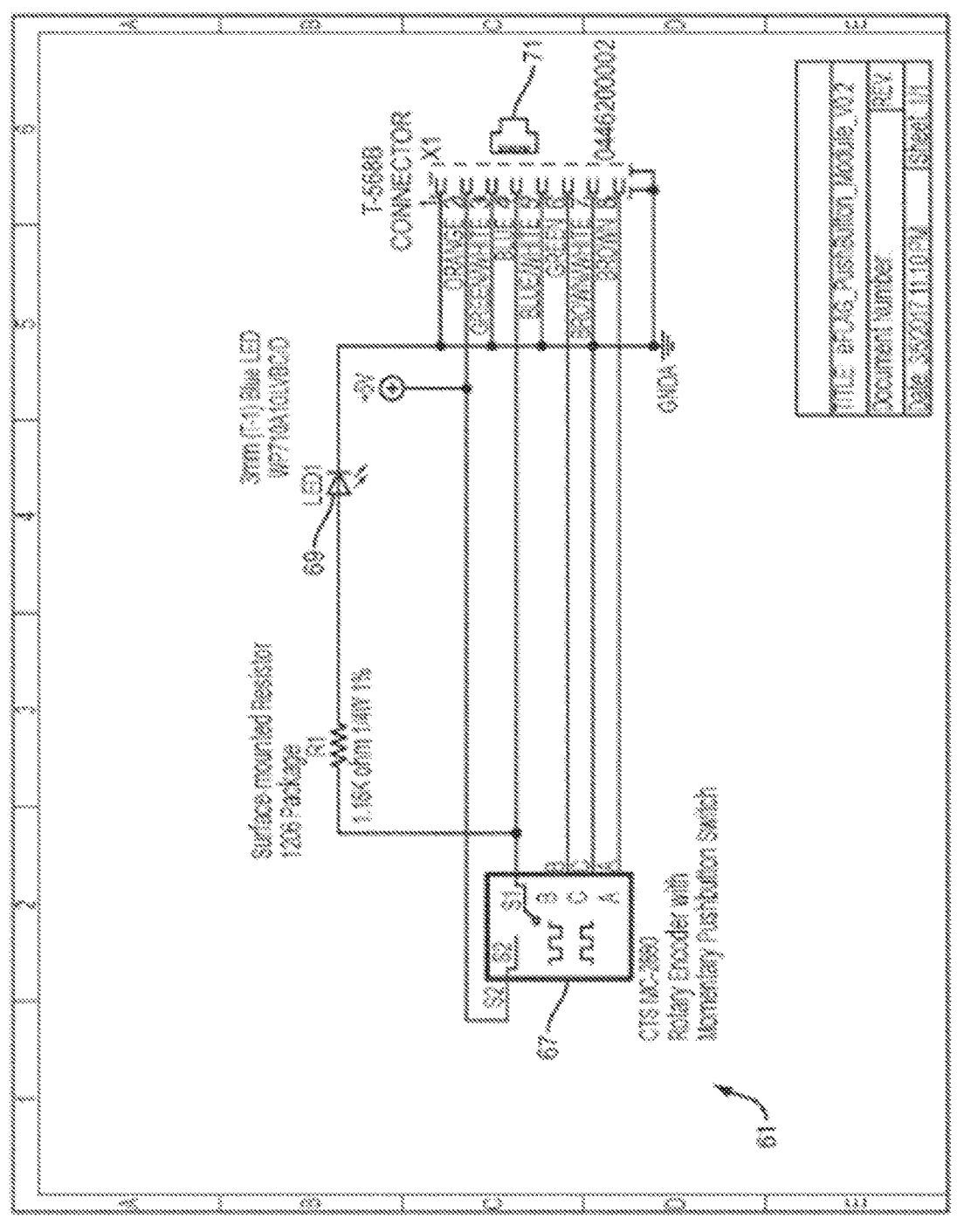
FIG. 8 shows an electrical schematic representation of the control device shown illustrated in FIGS. 7(a) and 7(b), according to certain embodiments of the disclosed subject matter herein.
Figure 9:
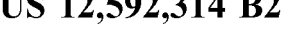
FIG. 9 shows a bottom plan view of the printed circuit board for the control device illustrated in FIG. 7(b), according to certain embodiments of the disclosed subject matter herein.
Figure 9:
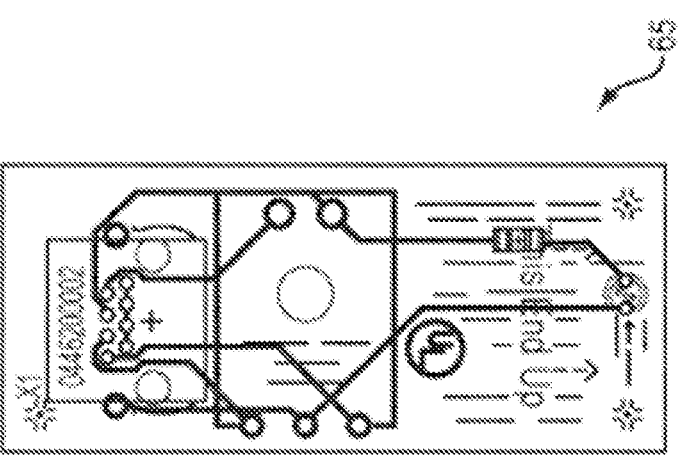

Referring now to FIGS. 3(*a*), 3(*b*), and 4, each visual status indicator 27 can comprise a light circuit 39 that is affixed to an outer housing 41, the construction of each to be described in detail below. The light circuit 39 can include a printed circuit board (PCB) 43 on which a pair of light emitting diodes (LEDs) 45-1 and 45-2 as well as an output connector 46 are mounted. The electrical schematic of the light circuit 39 is provided in FIG. 5. The wiring pattern for the printed circuit board 43 is provided in FIG. 6. In some embodiments, each LED 45-1 or 45-2 can be capable of generating multiple (e.g., seven) distinct colors for use within the eFLAG system 25. For instance, each LED 45-1 or 45-2 may be in the form of a 5 mm, clear, tri-color (red, green blue) through-hole LED.

The outer housing 41 can provide at least two functions, namely, (i) as a mount device to facilitate installation of the visual status indicators 27 (e.g., onto a conventional single gang electrical outlet box) and (ii) as an optical device to help disperse light illuminated from the LEDs 45. In some embodiments, the outer housing 41 can be formed as a unitary piece that is constructed of a suitably rigid and at least partially opaque material, such as plastic. However, it is to be understood that outer housing 41 could be alternatively constructed using multiple components formed from different materials.

In some embodiments, the outer housing 41 can comprise a generally rectangular cover plate 47 having a predominantly flat front surface 49-1 and a predominantly flat rear surface 49-2. The cover plate 47 can be appropriately dimensioned to mount onto a conventional, single-gang electrical outlet box (not shown). In some embodiments, the cover plate 47 can be provided with a pair of transverse circular openings 51 that are located in alignment with the pair of internally threaded, mounting bores formed in a conventional single-gang outlet box. In this manner, the cover plate 47 can be affixed to the outlet box by inserting screws through openings 51 and into threaded engagement with the corresponding bores in the outlet box.

In some embodiments, the outer housing 41 can also include a pair of hollowed light receptacles 53-1 and 53-2, each receptacle 53-1 or 53-2 being generally rectangular in transverse cross-section and projecting orthogonally away from the rear surface 49-2. Each receptacle 53 can be appropriately dimensioned to receive a corresponding LED 45 from the light circuit 39 and thereby direct or focus light illuminated therefrom towards the front of the outer housing 41. The receptacles 53 can be together shaped to include a pair of inwardly projecting, articulating latch fingers or snaps 55-1 and 55-2 which align for snap engagement within corresponding notches 56-1 and 56-2 formed in opposing ends of the printed circuit board 43. In this matter, the PCB 43 can be snapped in a reliably consistent orientation, affixed securely to the outer housing 41.

Figure 4:
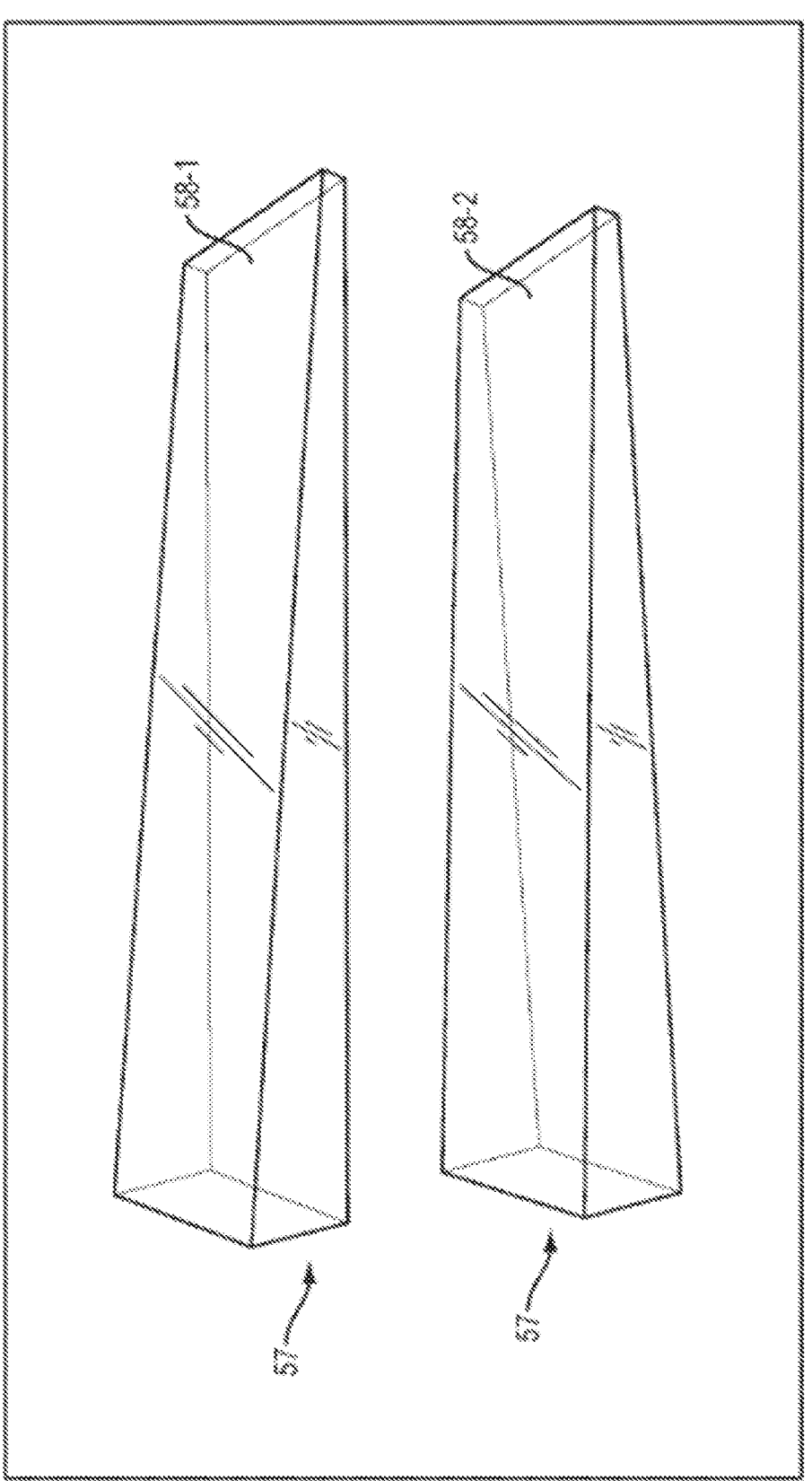
FIG. 4 shows a front perspective view of the pair of illumination blades illustrated in FIGS. 3(a) and 3(b), according to certain embodiments of the disclosed subject matter herein.

In some embodiments, the visual status indicator 27 can also comprise a pair of thin illumination blades 57-1 and 57-2 that are fittingly disposed within appropriately dimensioned openings in the cover plate 47 which are in optical communication with the receptacles 53-1 and 53-2, respectively. Each blade 57-1 or 57-2 can be mounted so as to project orthogonally out from the front surface 49-1 of the cover plate 47. Each blade 57-1 or 57-2 can have an elongated, wedge-shaped construction (i.e., trapezoidal in longitudinal cross-section), with at least one broad surface 58-1 having a roughened texture to help disperse light and thereby improve the visibility of light shone therethrough and an opposing surface 58-2 that is generally smooth, the distinction between surfaces 58-1 and 58-2 being seen in FIG. 4. As can be appreciated, light emitted from each LED 45 can be focused forward by its corresponding receptacle 53 and emanates throughout the exposed outer surfaces of the blade 57, primarily through the one or more roughened surfaces 58-1, to create a relatively dispersed and conspicuous color-based visual indicator.

As referenced earlier, the color shown through each of top and bottom blades 57-1 and 57-2 can be used to identify the treatment status of the patient assigned to an examination room 13. In this manner, the entire team of healthcare professionals assigned to the collection of rooms 13 can quickly and easily discern when he/she is responsible for performing a specified task in treating patients within the unit.

In some embodiments, the color emanating through one blade 57-1 or 57-2 (e.g., the top blade) can be used to indicate the status of the corresponding examination room 13, for example, when a certain medical professional, including the attending physician, is responsible for undertaking a particular task in connection with the treatment of the patient located within the corresponding examination room 13. For instance, a medical assistant, who typically handles certain preliminary treatment steps (e.g., gathering general patient data, taking vital signs, etc.), may be notified by illuminating the top blade 57-1 in a first color (e.g., magenta), whereas a nurse, who often handles final treatment steps (e.g., drawing blood samples, administering vaccines, etc.), may be notified by illuminating top blade 57-1 in a second color (e.g., red).

In some embodiments, the color emanating through another blade (e.g., the bottom blade 57-2) can be used to denote the specific healthcare provider (e.g., a particular physician) primarily assigned to treat the patient within the corresponding examination room 13. Because multiple healthcare providers typically cover a common unit, the bottom blade can be color-coded to designate primary patient examination responsibility amongst the team of healthcare providers. For instance, a first doctor may be designated using the color green and a second doctor may be designated using the color yellow.

In some embodiments, the light provided by the blade denoting the specific healthcare provider (e.g., a physician) may remain illuminated throughout examination of the patient. In this manner, this blade can continuously notify the healthcare team the particular physician responsible for the patient. Because each physician bears enhanced responsibilities in regard to the ultimate well-being of his/her patients, this blade via its color-coded light can create a constant and easily identifiable reminder to each physician of the patient rooms 13 that are directly under his/her care, as well as an indication to the staff of where that physician is in the event they have to urgently locate that physician.

To increase the visibility of either blade 57, in some embodiments, each LED 43 can be set to initially strobe at a defined rate when attendance is required. If the healthcare provider is delayed in attending to the patient beyond a predefined threshold, the LED 43 can be set to strobe at an increased rate to denote an increased sense of urgency. Once the proper healthcare provider attends to the patient, which can be confirmed by certain actions (e.g., depressing the control device 31 or accessing the patient records using the computing device 21 in the correspondence examination room 13), the strobing LED 43 can be set to stop flashing and illuminate a solid color to denote active treatment by the attending healthcare provider.

To improve guidance for a healthcare provider (e.g., a physician) when two or more examination rooms 13 contain patients waiting for that healthcare provider, in some embodiments, the eFLAG system 25 can be designed such that the LED 43 for the examination room containing the patient who has waited the longest is set to strobe faster than the LEDs for other examination rooms. In some embodiments, a healthcare team professional can perform certain actions (e.g., rotate its corresponding control device 31) to reset the faster-strobing LED 43 such that it will return to normal flashing. In some embodiments, that the LED 43 for the examination room containing the patient who has waited the next longest can be set to strobe faster than the LEDs for other examination rooms.

The functions of the top blade and the bottom blade are each configurable and can be exchanged.

IV. Control Device 31

Referring back to FIG. 2, each control device 31 can be installed outside its corresponding examination room 13, e.g., at a height convenient for user access while reducing the risk of inadvertent child-activation (in one example, approximately 58 inches above the floor). As noted previously, each control device 31 can be used to manually update the illumination state of its corresponding visual status indicator 27.

Referring now to FIGS. 7(a), 7(b), 8, and 9, each control device 31 can comprise a pushbutton circuit 61 that is affixed to a cover plate 63 to provide a largely modular construction. The pushbutton circuit 61 can include a printed circuit board (PCB) 65, shown in isolation in FIG. 9, onto which is mounted a pushbutton switch 67, a status LED 69, and an electrical connector 71, all of which are represented schematically in FIG. 8.

In some embodiments, the pushbutton switch 67 can include a rotary encoder with a momentary pushbutton switch, thereby allowing for switching amongst a plurality of defined positions or switching states, through the manual depression or uni-/bi-directional rotation of an enlarged actuation knob 73. For instance, the pushbutton switch 67 may be in the form of a Series 288 rotary encoder of the type manufactured by CTS Corporation.

The cover plate 63 can be a largely solid plate appropriately dimensioned to be mounted onto a conventional, single-gang electrical outlet box using screws. A small circular opening or window 75 on the cover plate 63 can allow LED 69 to at least partially project therethrough and thereby visually display the operability state of the pushbutton circuit 61. The cover plate 63 can also be shaped to define an enlarged, centralized circular bore 77 through which the rotor shaft of pushbutton switch 67 projects, with the actuation knob 73 mounted on its free end to facilitate actuation.

V. Central Control Circuit 29

Referring back to FIG. 1, each visual status indicator 27, control device 31, occupancy sensor 33, and door sensor 35 within a designated unit can be electrically coupled to the central control circuit 29, which can be located in the team administration center 15 for that unit. The central control unit 29 can be electronically coupled with the computer network 17 and the EHR controller 23. As a result, the central control circuit 29 is able to operate in conjunction with the computer network 17 and the EHR controller 23 to control and regulate the operation of the eFLAG system 25, as well as to convey the statuses of examinations rooms 13 via the computer network 17 and the EHR controller 23.

For example, via the communication with the EHR controller 23, the eFLAG system 25 can change the color emanating through a blade (e.g., the top blade) to indicate a room status change when a certain medical professional logs into the computing device 21-1 in the examination room 13-1 without the medical professional's manual operation of the control device 31-1, change the color emanating through a blade (e.g., the top blade) to indicate that a healthcare team professional using the computing device 21-2 has requested another healthcare team professional to come and provide help in the examination room 13-2, or change the color emanating through a blade (e.g., the bottom blade) to denote the specific healthcare provider (e.g., a particular physician) primarily assigned to treat the patient within the corresponding examination room 13-n as a result of the healthcare team professional using the computing device 21-n in the examination room 13-n to look up the record of a patient for that healthcare provider.

In some embodiments, receipt of the statuses of the examination rooms 13 by the EHR controller 23 also enable the ability, among other things, to display a visual representation of all of the exam rooms and their statuses, display the location and status of each patient in the healthcare provider's daily schedule, automatically add documentation of accurate face-to-face visit times for the healthcare provider which is often used for billing purposes, calculate accurate anticipated waiting times for patients, and report on resource efficiency and productivity in order to optimize resources and productivity.

In some embodiments, the central control circuit 29 can comprise a programmable processor 101, at least one LED driver circuit 81 in connection with a connector 46 of each visual status indicator 27 (e.g., via a Cat5e Ethernet cable), at least one switch multiplexer 83 in connection with a connector 71 of each control device 31 (e.g., via Cat5e Ethernet cable), and a network patch panel 85 in connection with the computer network 17, each of the sensors 33 and 35, and the output of each LED driver circuit 81 and switch multiplexer 83 (e.g., via Cat5e Ethernet cable).

As referenced briefly above, the LED driver circuit 81 can be electrically coupled to the connector 46 for each visual status indicator 27 and can be responsible for, among other things, regulating the supply of power to LEDs 45. In this sense, the LED driver circuit 81 can control, in part, the illumination state of each visual status indicator 27.

Figure 10:
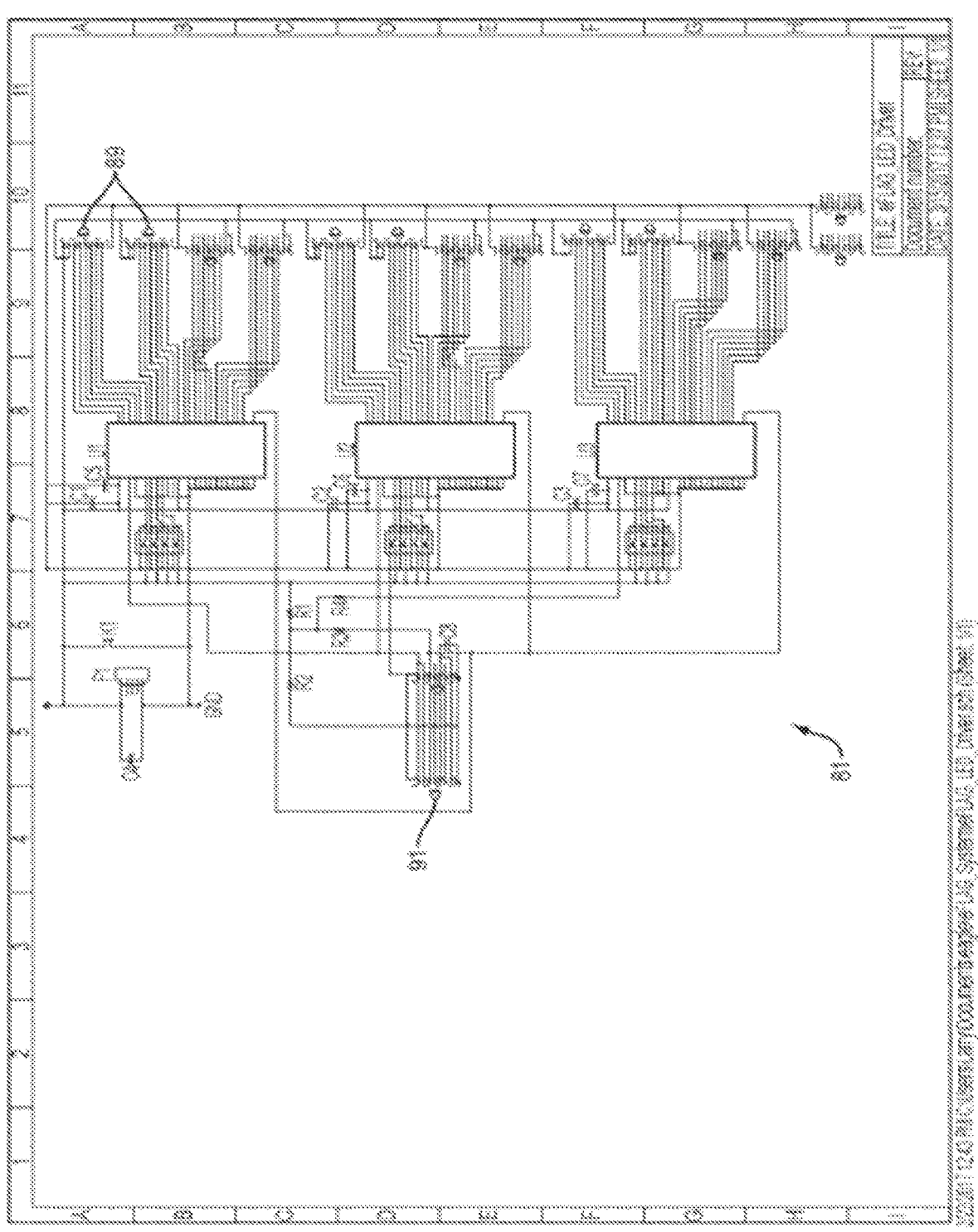
FIG. 10 shows an electrical schematic representation of the LED driver illustrated in FIG. 1, according to certain embodiments of the disclosed subject matter herein.
Figure 11:
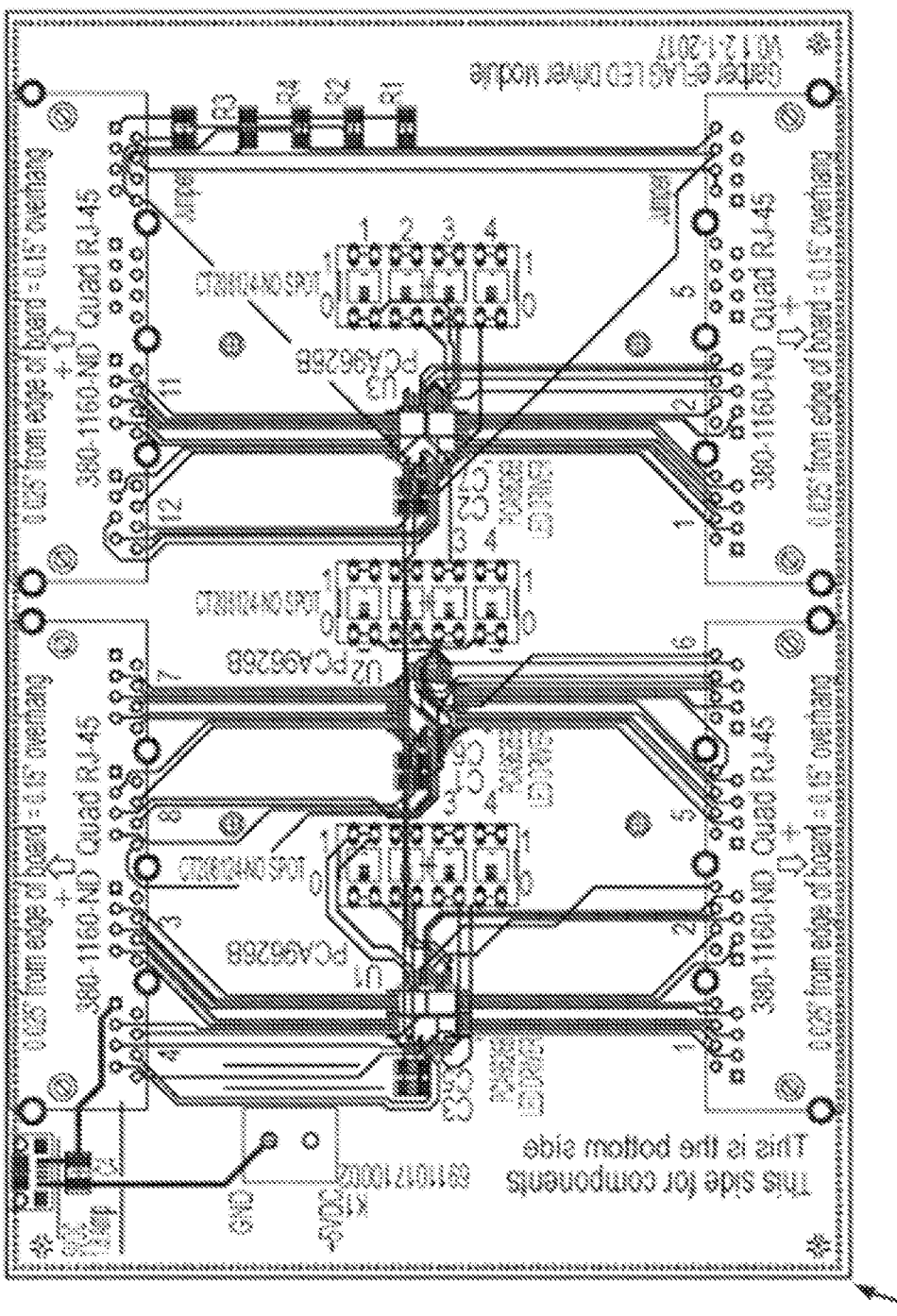
FIG. 11 shows a bottom plan view of the printed circuit board for the LED driver illustrated in FIG. 10, according to certain embodiments of the disclosed subject matter herein.

In some embodiments, the LED driver circuit 81 can include a printed circuit board (PCB) 87, on which are mounted, inter alia, a plurality of input connectors 89, each of which is connected to the PCB 43 of a corresponding visual status indicator 27, and an output connector 91 which is connected to the network patch panel 85. An electrical schematic of the LED driver circuit 81 is in FIG. 10 and a wiring pattern for the PCB 87 is in FIG. 11.

In some embodiments, the switch multiplexer 83 can be electrically coupled to the pushbutton switch 67 and the sensors 33 and 35, and can be responsible for, among other things, monitoring the switch status of each control device 31 and the statuses of the sensors 33 and 35. By connecting each control device 31 and sensors 33 and 35 to the network patch panel 85 via the switch multiplexer 83, the healthcare facility 11 can be wired in a more cost-efficient and readily scalable fashion.

Figure 12:
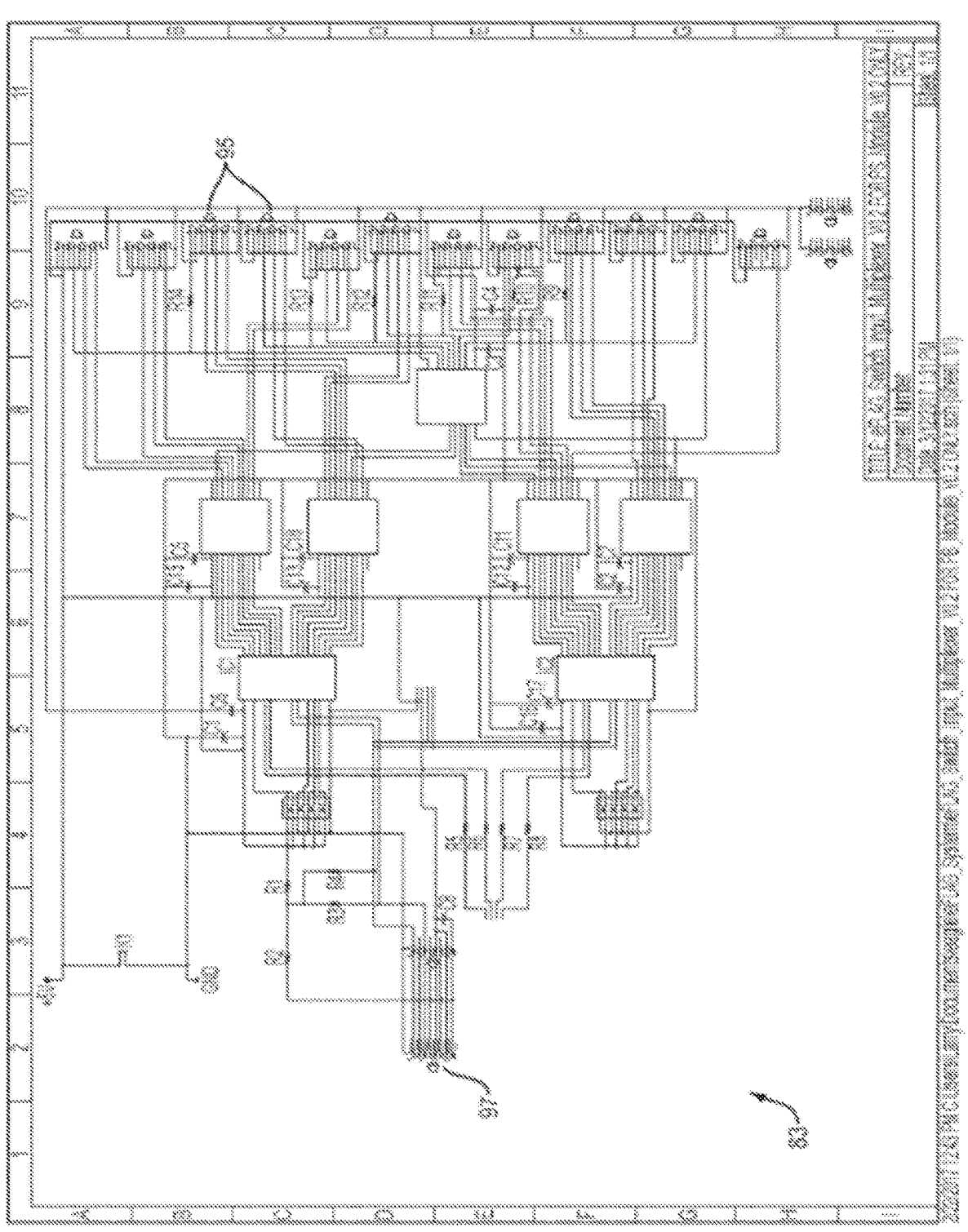
FIG. 12 shows an electrical schematic representation of the switch multiplexer illustrated in FIG. 1, according to certain embodiments of the disclosed subject matter herein.
Figure 13:
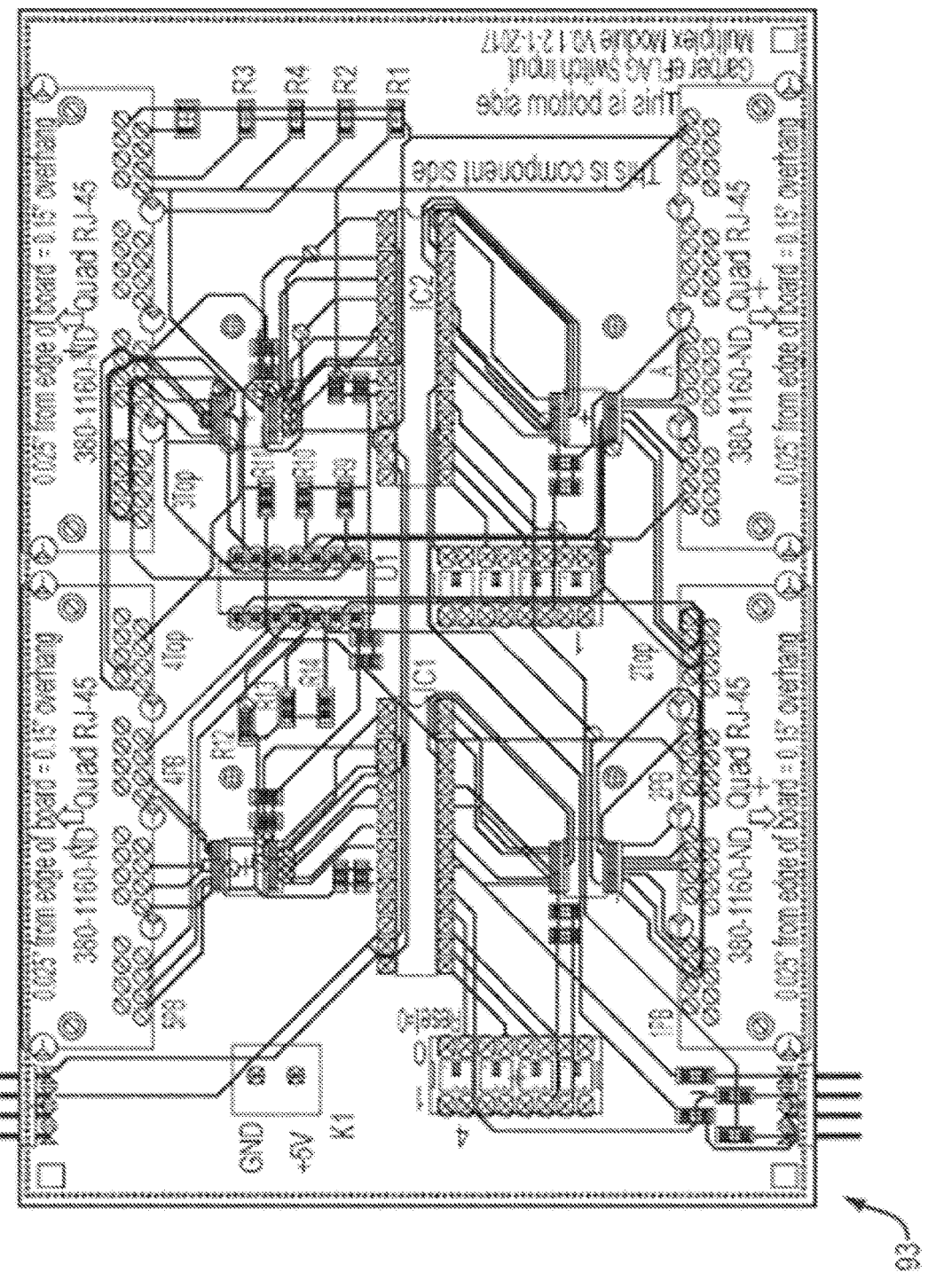
FIG. 13 shows a bottom plan view of the printed circuit board for the switch multiplexer illustrated in FIG. 12, according to certain embodiments of the disclosed subject matter herein.

In some embodiments, the switch multiplexer 83 can include a printed circuit board 93, on which are mounted, inter alia, a plurality of input connectors 95, each of which is connected to the PCB 65 of a corresponding control device 31, and a single output connector 97, which is connected to the network patch panel 85. An electrical schematic of the switch multiplexer 83 is in FIG. 12 and a wiring pattern for the PCB 93 is in FIG. 13.

In some embodiments, the network patch panel 85 can be disposed in the team administration center 15 (e.g., within a cabinet or other physical structure that affords protection and suitable airflow) and provide an easy-to-manage solution for connecting together the complex electrical network for the eFLAG system 25. For example, the network patch panel 85 can be a RJ45-type patch panel.

In some embodiments, the programmable processor 101 (e.g., a single board, Raspberry Pi compute device) can be connected to each of the network patch panel 85, the LED driver circuit 81, and the switch multiplexer 83, and is responsible for controlling the operation of the eFLAG system 25. In other words, the programmable processor 101 can be specifically programmed to manage and customize operation of the eFLAG system 25.

Figure 14:
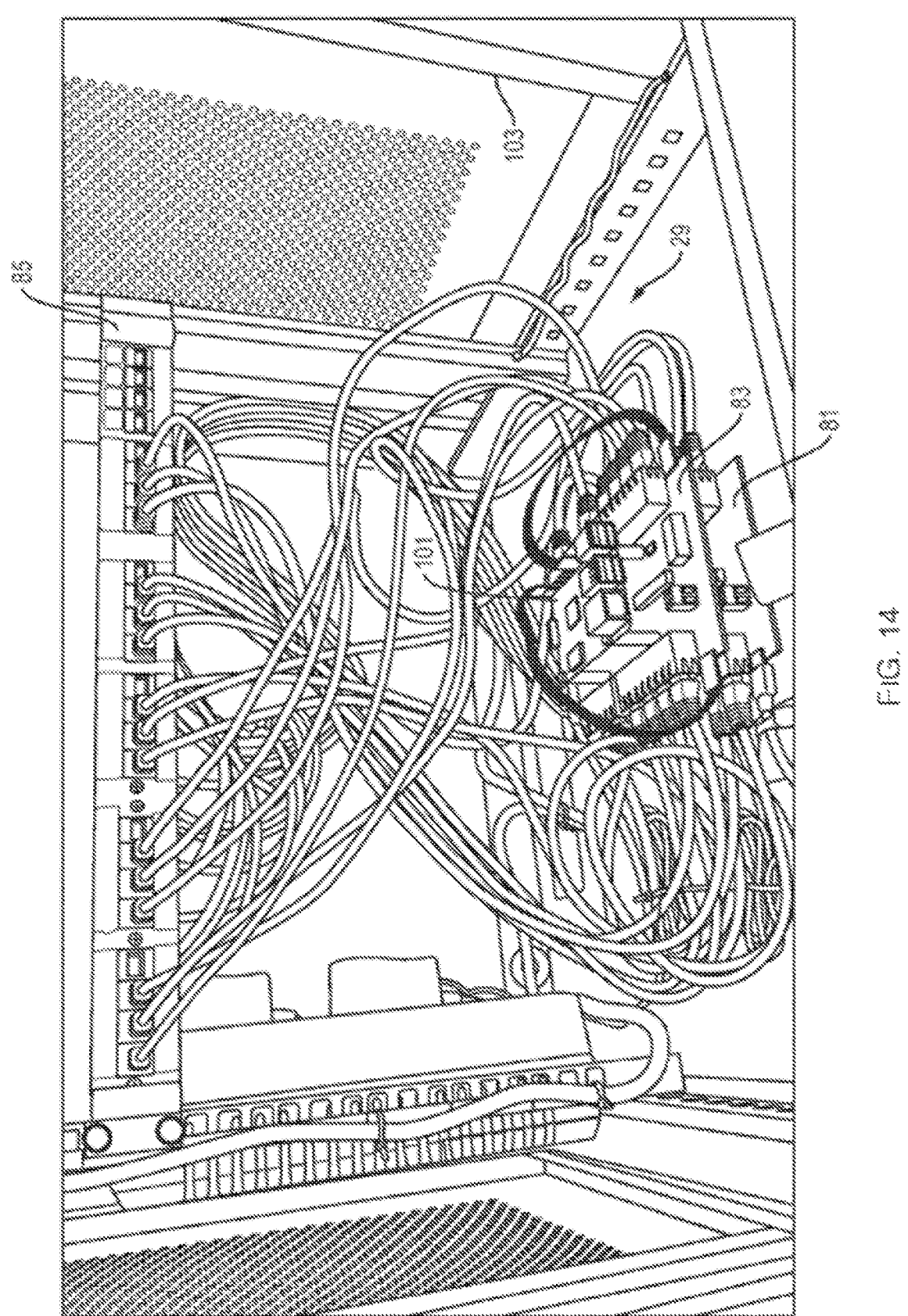
FIG. 14 depicts one configuration of the housing and electrical wiring for the central control circuit illustrated in FIG. 1, according to certain embodiments of the disclosed subject matter herein.
Figure 15:
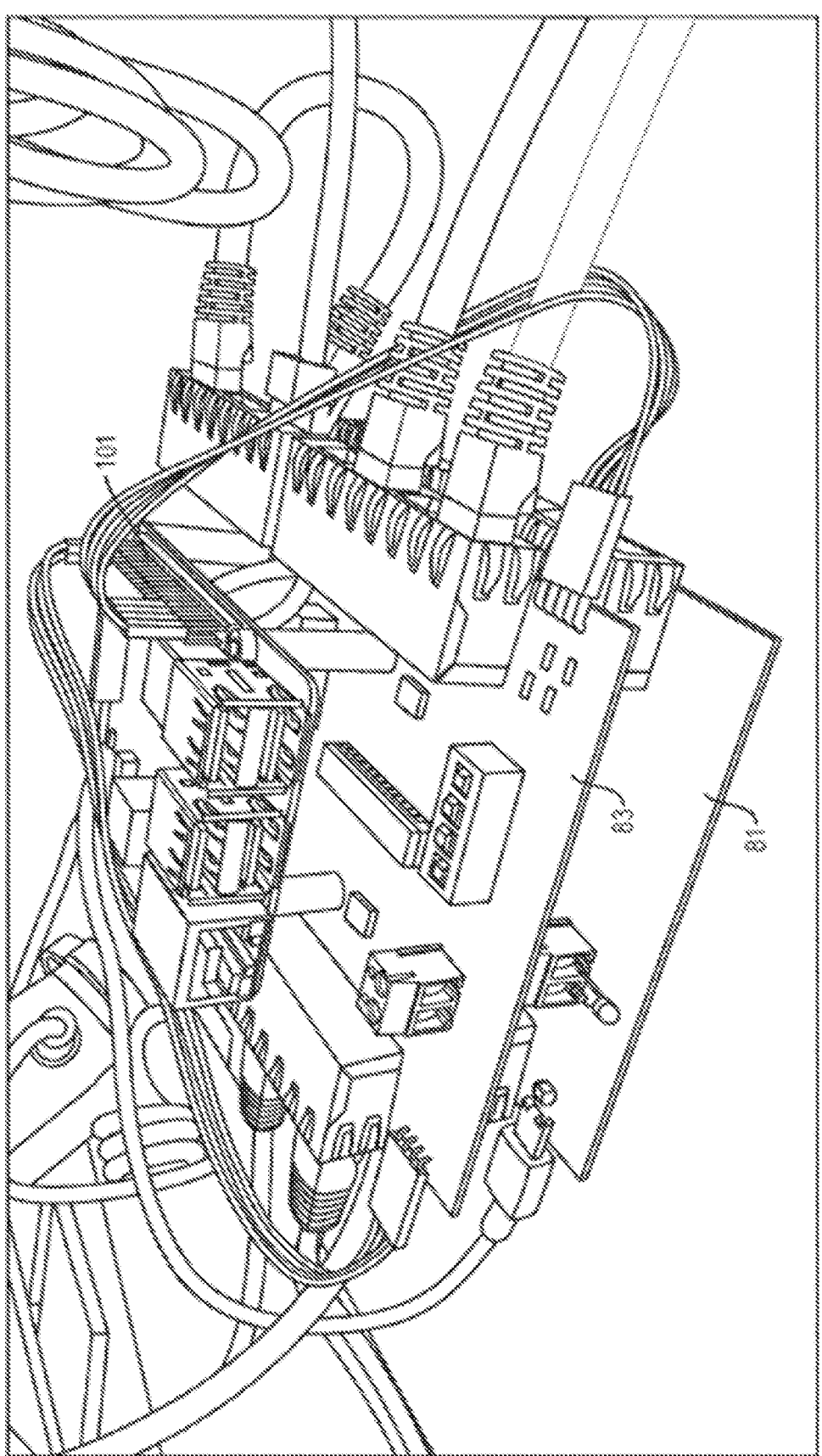
FIG. 15 depicts one configuration of stacked processor, LED driver and switch multiplexer illustrated in FIG. 14, according to certain embodiments of the disclosed subject matter herein.

FIG. 14 represents one possible arrangement of the housing and electrical wiring for the central control circuit 29. For example, the central control circuit 29 can be housed within a cabinet 103 that provides suitable air flow. In some embodiments, the processor 101, the switch multiplexer 83, and the LED driver circuit 81 can be arranged in a stacked configuration to facilitate electrical interconnection and to minimize overall footprint, as illustrated in FIG. 15. Referring back to FIG. 14, the network patch panel 85 can be separately mounted within the cabinet 103 and can be identified with labelled markings to designate the specific room and component to which each cable jack electrically connects.

The central control circuit 29 can be readily scalable to accommodate a greater number of units and/or examination rooms 13 within each unit. For instance, the central control circuit 29 could be modified to accommodate a greater number of exam rooms 13 by simply stacking and electrically connecting a single processor 101 to multiple LED driver circuits 81 and multiple switch multiplexers 83. In this manner, the central control circuit 29 can be increased in scale without increasing its overall footprint.

VI. Sample Cycle of Patient Treatment Status Notifications

Figure 16:
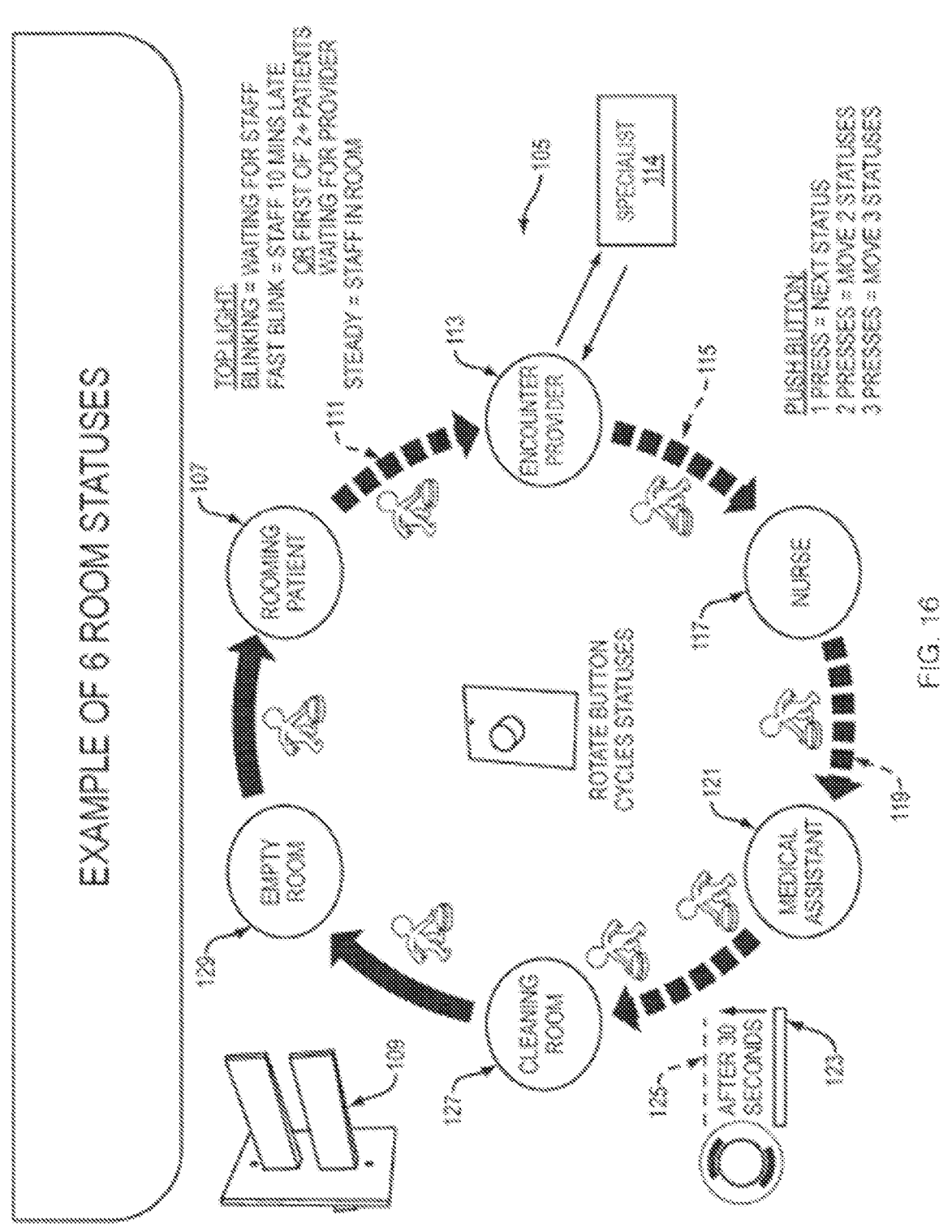
FIG. 16 illustrates one possible cycle of patient treatment status notifications which can be implemented using the patient treatment status notification system illustrated in FIG. 1, according to certain embodiments of the disclosed subject matter herein.

As explained above, the eFLAG system 25 can be configured to provide a unique, user-intuitive way of providing the real-time patient care status to a designated team of healthcare professionals. Referring now to FIG. 16, a sample cycle or chain of treatment statuses is represented generally by reference numeral 105.

As the first step in the treatment process, a patient checks into the healthcare facility 11 and identifies the nature of the visit. The aforementioned registration process is either initiated by (i) the patient (e.g., using a compatible software application, such as the MyChart mobile application or the Welcome application running on a kiosk) or (ii) an office administrator present at the healthcare facility 11.

After check-in, the healthcare facility 11 can designate an examination room 13 for the patient in accordance with a predefined room assignment hierarchy (e.g., based on order of registration, nature of visit, patient urgency, room availability, etc.). Once an examination room 13 is available and has been assigned to the patient, activation of the eFLAG system 25 can commence upon either (i) entry into the examination room 13, which can be recognized by sensors 33 and/or 35 in the examination room 13, (ii) access of the patient health records via the computing device 21 in the examination room 13, or (iii) manual activation of the control device 31 (e.g., thru depression of the actuation knob 73) associated with the examination room 13. As a result, the top blade 57-1 of the visual status indicator 27 can display the color assigned to the "rooming" status (e.g., magenta), as represented by reference numeral 107 in FIG. 16.

With the patient in the room, as represented by reference numeral 107, compilation of certain patient-related data may be undertaken by a member of the healthcare team. All health-related data can be uploaded onto the electronic health records software (e.g., an EHR system) installed on the computer network 17.

Based on certain factors, such as physician availability and/or prior relationship, the computer network 17 can recognize a designated physician for the patient. As a result, the bottom blade 57-2 of the visual status indicator 27 can display the color pre-assigned to that physician (e.g., green), as represented by reference numeral 109 in FIG. 16.

As the healthcare team professional exits the examination room 13, they can activate the eFLAG system 25, for example, by depressing or rotating the actuation knob 73 on the control device 31 associated with the examination room 13. As a result, the top blade 57-1 of the visual status indicator 27 can display the color assigned to represent a healthcare provider (e.g., green), and will be blinking to designate a "waiting for provider" status, as represented by reference numeral 111 in FIG. 16.

Upon arrival at the examination room, the physician can activate the eFLAG system 25, for example, by depressing the actuation knob 73 on the control device 31 or through accessing the patient health records using the computing device 21. As a result, top blade 57-1 stops flashing and illuminates in the solid color representing a healthcare provider (e.g., green for physician), while the bottom blade 57-2 continues to display the specific physician's pre-determine color, thereby notifying other professionals within the healthcare team that the patient is currently being evaluated by the designated physician, as represented by reference numeral 113.

The assigned physician then engages in the primary examination of the patient. After finishing examination of the patient, the doctor electronically signifies completion of his/her responsibilities within the treatment process, for example, by activating the control device 31 upon departure from the room or by simply signing out of the electronic health records software from the computing device 21.

A single depression of the actuation knob 73 on the control device 31 can activate the top blade 57-1 of the visual status indicator 27 in the color designated for the next professional in the treatment cycle 105. In the present example, a nurse is designated as the next professional in treatment cycle 105 and is represented by the color red. Accordingly, when the physician transfers responsibility to the nurse (e.g., to obtain a blood sample), the top blade 57-1 of the visual status indicator 27 can initially strobe at a defined rate to indicate that his/her presence is required, as represented by reference numeral 115. Upon detecting arrival of the nurse (e.g., through activation of the control device 31), the eFLAG system 25 can illuminate the top blade 57-1 of the visual status indicator 27 solidly in the designated color (e.g., red in this example), as represented by reference numeral 117.

In the present example, the cycle 105 can transition from the nurse to a medical assistant (e.g., to complete the treatment and check-out process). Accordingly, in the sample cycle 105, the eFLAG system 25 can display the transition in responsibility by illuminating the top blade 57-1 of the visual status indicator 27 as a flashing blue color, as represented by reference numeral 119. As noted previously, the top blade 57-1 may strobe at an increased rate after a predefined period of time to denote an increased sense of urgency in tending to the patient.

Once the medical assistant attends to the patient, the medical assistant can activate the eFLAG system 25 (e.g., by depressing the actuation knob 73 on the control device 31). As a result, the top blade 57-1 of the visual status indicator 27 can stop flashing and illuminate in the solid blue color assigned to the medical assistant, as represented by reference numeral 121.

In the present example, the medical assistant finishes the visit. Accordingly, in the sample cycle 105, the eFLAG system 25 can display the transition to the patient dressing and exiting the room by illuminating the top blade 57-1 of the visual status indicator 27 as a solid yellow color, as represented by reference numeral 123.

When the patient completes dressing and leaves the room, the eFLAG system 25 can recognize this action with sensors 33 and/or 35 in the examination room 13 and in the present example, the top blade 57-1 can start flashing the yellow color to alert that the examination room 13 is now empty and ready for cleaning, as represented by reference numeral 125. The eFLAG system 25 can also turn off the light on the bottom blade 57-2 of the visual status indicator 27 because that healthcare provider is no longer associated with that the examination room 13.

Once the medical assistant returns to the examination room 13 to clean it, the medical assistant can activate the eFLAG system 25 (e.g., by depressing the actuation knob 73 on the control device 31). As a result, the top blade 57-1 of the visual status indicator 27 can stop flashing and illuminate in the solid yellow color assigned to the status of cleaning the room, as represented by reference numeral 123.

In the present example, the sample cycle 105 transitions from the cleaning the room to the room being empty when the medical assistant activates the eFLAG system 25, for example, by depressing the actuation knob 73 on the control device 31 associated with the examination room 13. As a result, the top blade 57-1 of the visual status indicator 27 can shut the light off, designating that the examination room 13 is now empty, clean, and ready for the next patient, as represented by reference numeral 129.

In the present example, the eFLAG system 25 is designed to cycle amongst a team of three professionals in a specified circular order. In other words, the eFLAG system 25 is configured in a pattern that continuously cycles from the medical assistant, to the physician, to the nurse, and then back to the medical assistant, as shown in FIG. 16.

However, as referenced above, the treatment cycle 105 need not be limited to any particular number, type, or order of healthcare professionals. Rather, the particular number, type, and arrangement of healthcare professionals within the sample cycle 105 could be modified to fit various needs.

It is also to be understood that the transfer of responsibilities involved in the treatment of a patient need not always proceed in the specific order defined in the sample treatment cycle 105. Rather, the transfer of responsibilities amongst a team of healthcare professionals is largely dictated by the particular needs of the patient. Accordingly, the eFLAG system 25 is designed to allow for the transfer of responsibility from one professional in the healthcare team to any other professional in the healthcare team by actuating the control device 31 as many times as required to skip to the required person in the cycle.

For instance, if a physician determines that a particular step would be most effectively served by the medical assistant, the physician can skip over the nurse in treatment cycle 105 by depressing the actuation knob 73 on the control device 31 two times. As a result, the visual status indicator 27 would switch from illuminating the color code associated with the physician on the top blade 57-1 to illuminating the color code associated with the medical assistant on the top blade 57-1. In this manner, the chain of patient treatment can be modified, as needed, to suit the needs of each patient.

Healthcare team professionals can also move one or more steps forward or backwards in the treatment cycle 105 by rotating the actuation knob 73 on the control device 31 clockwise or counterclockwise, respectively. Recognizing that depressing the actuation knob 73 may inadvertently also rotate the actuation knob, the eFLAG system 25 can be designed to ignore spurious rotations of the actuation knob 73 on the control device 31.

Through this design, it is to be understood that each professional in the healthcare team can readily assess patient examination status, in real time, by monitoring the illumination state of each visual status indicator 27 within the team unit. If/when a designated blade 57 in any visual status indicator 27 flashes in his/her assigned color, the healthcare professional intuitively recognizes immediate responsibility for a specified treatment task, the details of which may be ascertained via electronic health records accessed via the computer network 17.

It should be noted that the sample cycle 105 discussed above is provided for illustrated purposes only. As such, it is to be understood that numerous variations to the sample cycle 105 could be implemented according to different embodiments of the disclosed subject matter herein. For example, one or more new treatment steps can be added into the treatment cycle; one or more treatment steps can be removed from the treatment cycle; one or more treatment steps can be changed or rearranged in the treatment cycle.

In some embodiments, the eFLAG system 25 can also support one or more out-of-cycle steps to be associated with a treatment cycle 105. For example, referring to FIG. 16 again, after initiation examination, a healthcare provider 113 (e.g., a physician) can refer the patient to see another healthcare provider 114 (e.g., a specialist). After the specialist 114 has tended the patient, the treatment of the patient can return back to the physician 113. Similarly, other healthcare team professionals can be requested to temporarily join a healthcare provider 113 (e.g., a physician) in the examination room 13. In one example, the visual status indicator 27 would change from illuminating the color code associated with the physician on one blade (e.g., the top blade 57-1) to alternately also illuminating the color code associated with the requested healthcare team professional. When the requested healthcare team professional arrives at the examination room 13, they can activate the eFLAG system 25 (e.g., by depressing or rotating the actuation knob 73 on the control device 31). As a result, one of the blades (e.g., the top blade 57-1) of the visual status indicator 27 can stop flashing and illuminate in the color code associated with the physician, thereby letting other healthcare team professionals know that the physician's request has been satisfied.

In some embodiments, integration of the eFLAG system 25 with the EHR system can enable healthcare providers to interact with the eFLAG system 25 through keywords or commands (e.g., SmartLinks) of the EHR system, which can be entered using a computing device 21 in the examination room 13 or other computing devices connected to the computer network 17. For example, a staff can enter .FlagLab to indicate the patient is going to the lab, .FlagRad to indicate the patient is going to the radiology department, .FlagWaitingroom to indicate the patient is in the waiting room, .FlagBreastfeeding to indicate the patient is to be left alone in the exam room while she breastfeeds her infant, or .FlagTreatment to indicate the patient is undergoing a treatment such as intravenous hydration or an albuterol nebulizer. Use of these keywords or commands of the EHR system in this way can cause the eFLAG system 25 to modify its function or display of status. For example, when FlagBreastfeeding is entered into the computing device 21-1 in the examination room 13-1, the eFLAG system 25 can cause one blade (e.g., the top blade 57-1) of the visual status indicator 27-1 to display a constant room-occupancy patient status color 123 until the door sensor 35-1 is activated while ignoring the occupancy sensor 33-1. Similarly, in another example, when .FlagTreatment is entered into the computing device 21-1 in the examination room 13-1, the eFLAG system 25 can cause one blade (e.g., the top blade 57-1) of the visual status indicator 27-1 to flash status color 115 every 10 minutes to remind a nurse to check on the patient, with the blade of the visual status indicator 27-1 displaying a constant status color 117 every time the nurse arrives to check the patient by depressing or rotating the actuation knob 73 on the control device 31.

VII. Features of the Disclosed Subject Matter

The design of the eFLAG system 25 disclosed herein introduce a number of features over traditional healthcare facility notification systems, according to certain embodiments.

As the first example, the eFLAG system 25 has integration that enables receipt of information from the computer network 17 and the EHR controller 23. As a result, changes in patient treatment status can, in part, be automatically detected by the eFLAG system 25 through routine steps involving normal use of the computer network 17, thereby creating a notification system that is significantly easy to operate and fault tolerant. For instance, the color emanating through the bottom blade 57-2 of the visual status indicator 27, which denotes the specific physician assigned to treat the patient within the corresponding examination room 13, is set correctly and automatically as a byproduct of a healthcare team professional using the computing device 21 in the examination room 13 to look up the record of the patient for that physician. Similarly, a healthcare provider can change the color emanating through the top blade 57-1 of the examination room's visual indicator status 27 to indicate that healthcare provider is in the room simply by logging into the computing device 21 in the examination room 13. For another instance, access of the EHR controller 23 can trigger more complex statuses, such as treatments which require reminders to nurses every 10 minutes, or to request specific staff to come to the examination room, for example, causing the top blade to blink alternating colors of the staff member requested and healthcare team professional already in the room. Pressing the control device 31 can stop the blinking so other staff members know they don't need to respond. Integration with the EHR controller can also allow for every treatment status to be set via the EHR system so staff with disabilities can take advantage of all of the eFLAG system's capabilities, e.g., by entering a SmartLink instead of reaching and activating the physical rotary button.

As the second example, the eFLAG system 25 has integration that enables sending communication to the computer network 17 and the EHR controller 23. As a result, changes in patient treatment status are communicated more accurately than would otherwise be possible relying solely on proxy measures such as logging in and out of a computer in the examination room or real-time location systems that don't know the healthcare professional's intent when they leave a room, such as whether they plan to return or who the next person needed in the room is. The high level of data accuracy enabled by this integration makes it possible to display detailed room statuses on team-wide displays ("TeamBoard") and individual healthcare provider schedules. It can also enable calculation and display of accurate anticipated wait times for patients or face-to-face time documentation for healthcare provider billing. In one instance, the integration with the EHR controller allows the TeamBoard to display length of time in a given status, with highlights to show excessive lengths of time in that status. Integration with the EHR controller can also allow for these highlights to account for the scheduled visit length. For another instance, integration with the EHR controller 23 can allow manual or automatic notification of staff (e.g., via their smartphones) about room status changes or requests, supplemented by EHR data such as orders that have already been entered.

As the third example, the eFLAG system 25 leverages room sensors 33 and 35 to optimize the efficient use of the examination rooms 13. For instance, when a patient is left alone in the examination room 13 to get dressed and leave on his/her own, the eFLAG system 25 can, for example by detecting the door is reopened and/or no occupancy is detected, automatically recognize an empty room and activate the top blade 57-1 of the visual status indicator 27 to blink a specific color indicating that the room is empty and ready for cleaning, even if the patient closes the door after they leave, without the need for making a patient wear an expensive and impersonal tag typical of real-time location systems.

As the fourth example, the eFLAG system 25 includes an easily discernable and user-intuitive means for determining the real-time patient treatment status and healthcare provider location across an entire unit of examination rooms 13. Simple visual cues guide healthcare professionals towards the examination room that they need to go into next. For instance, a rapidly blinking physician light which automatically activates if the patient has waited too long, alerts both the medical assistant to enter the room and ask the patient if they need anything while waiting for the physician, as well as the physician to hurry up to get into that room. Accordingly, the healthcare facility 11 is able to provide prompt, effective and satisfying patient care with great efficiency. In one instance, when multiple examination rooms have patients waiting, the visual status indicator can blink faster for the examination room containing the patient who has waited the longest. The staff can have the option to reset the waiting status (e.g., via the control device 31) for that examination room, e.g., to put it to the back of the waiting line, so the physician can be directed to first visit a patient that won't take long instead of a patient with lengthy problems.

As the fifth example, the eFLAG system 25 is easily scalable and therefore able to accommodate use in wide variety of different healthcare environments. Most notably, each visual status indicator 27 can be used to signal a large quantity of distinct professionals within a designated healthcare team. Furthermore, the design of the eFLAG system 25 allows for multiple units, each consisting of a considerable number of examination rooms 13, to be all linked together to provide a consolidated approach for monitoring the well-being of patients within a relatively large treatment facility.

As the sixth example, the eFLAG system 25 is highly configurable for each healthcare team within a diverse healthcare facility 11. Healthcare teams can easily configure the quantity, order, and types of statuses applicable to their team. They can choose which colors indicate which statuses and which healthcare providers. They can choose which statuses require blinking lights, how fast those lights should blink, whether the blinking should speed up after a period of time, how long that period of time should be, and how much faster the blinking should be.

As the seventh example, the eFLAG system 25 uses a representation of room statuses which can be intuitively manipulated by the control devices 31 and/or via integration with the EHR controller 23. The eFLAG system 25 can use one or more of three paradigms to represent room statuses: 1) the standard workflow cycle, 2) out-of-cycle statuses, and 3) add-on statuses. The standard workflow cycle can consist of two or more room states that can by stepped forward through by depressing the actuation knob 73 on the control device 31. Single-clicks, double-clicks, and triple-clicks of the actuation knob 73 on the control device 31 can intuitively and efficiently advance through 1, 2 or 3 statuses, respectively. Similarly, clockwise rotation of the actuation knob 73 on the control device 31 can intuitively and efficiently advance forward through the workflow cycle, while counter-clockwise rotation moves backwards to prior statuses in the workflow cycle. This can allow for common workflow cycle paths to be accomplished easily with a single depression of the actuation knob 73 on the control device 31, while the same actuation knob 73 on the control device 31 can be used to jump to any other status. In some embodiments, the same action that advances from status to status also returns to the first status when done with the last status. The eFLAG system can both reflect the current state and indicate the state coming next. In addition, the visual representation of a workflow cycle can match the physical motion of rotating the actuation knob 73 on the control device 31, making it easier to learn and more natural to use. In some embodiments, a user can readily actuate this single actuation knob 73 on the control device 31 without having to find it among a cluster of other actuators. Furthermore, in some embodiments, having a single actuator instead of multiple one can minimize the use of precious wall space. The second paradigm of room statuses includes the ability to jump at any moment to any number of optional "Out of Cycle" statuses. This allows for an almost unlimited number of less common states without interfering with the efficiency of the standard workflow cycle. The third paradigm of room statuses includes the ability to "add-on" a second status to the current status. This reflects the reality that during the course of the standard workflow cycle, it is not unusual to need the assistance of another healthcare professional. These simple and logical paradigms can be enacted through the use of the actuation knob 73 on the control device 31 and/or the computing device 21 that communicates with the EHR controller 23, and they can be visually displayed through combinations of the visual status indicators 27 or within the EHR or on a "TeamBoard" which shows the status of all examination rooms.

As the eighth example, the eFLAG system 25 is able to accurately identify the amount of time a healthcare provider spends face-to-face with a patient and convey this information in real time to an EHR system via the EHR Controller 23. This enables the EHR system to facilitate the use of time-based billing for patient encounters which affords the opportunity for maximizing revenue to reflect the actual billable work that was performed.

As the ninth example, the eFLAG system 25 is able to compile accurate historical data relating to the transfer of patient care amongst a healthcare team. For instance, by reviewing such data, the healthcare facility 11 can evaluate the rate of treatment provided by certain teams in order to discover, and potentially resolve, any staff or resource deficiencies or excesses.

VIII. Alternate Embodiments and Design Modifications

The embodiments shown above are intended to be examples only and those skilled in the art will be able to make numerous variations and modifications to it without departing from the spirit of the disclosed subject matters herein. All such variations and modifications are intended to be within the scope of the disclosed subject matters herein as defined in the appended claims.

For instance, the eFLAG system 25 could be modified, as needed, to provide the healthcare facility 11 with a simple and effective way for initiating an emergency alert condition.

Figure 17:
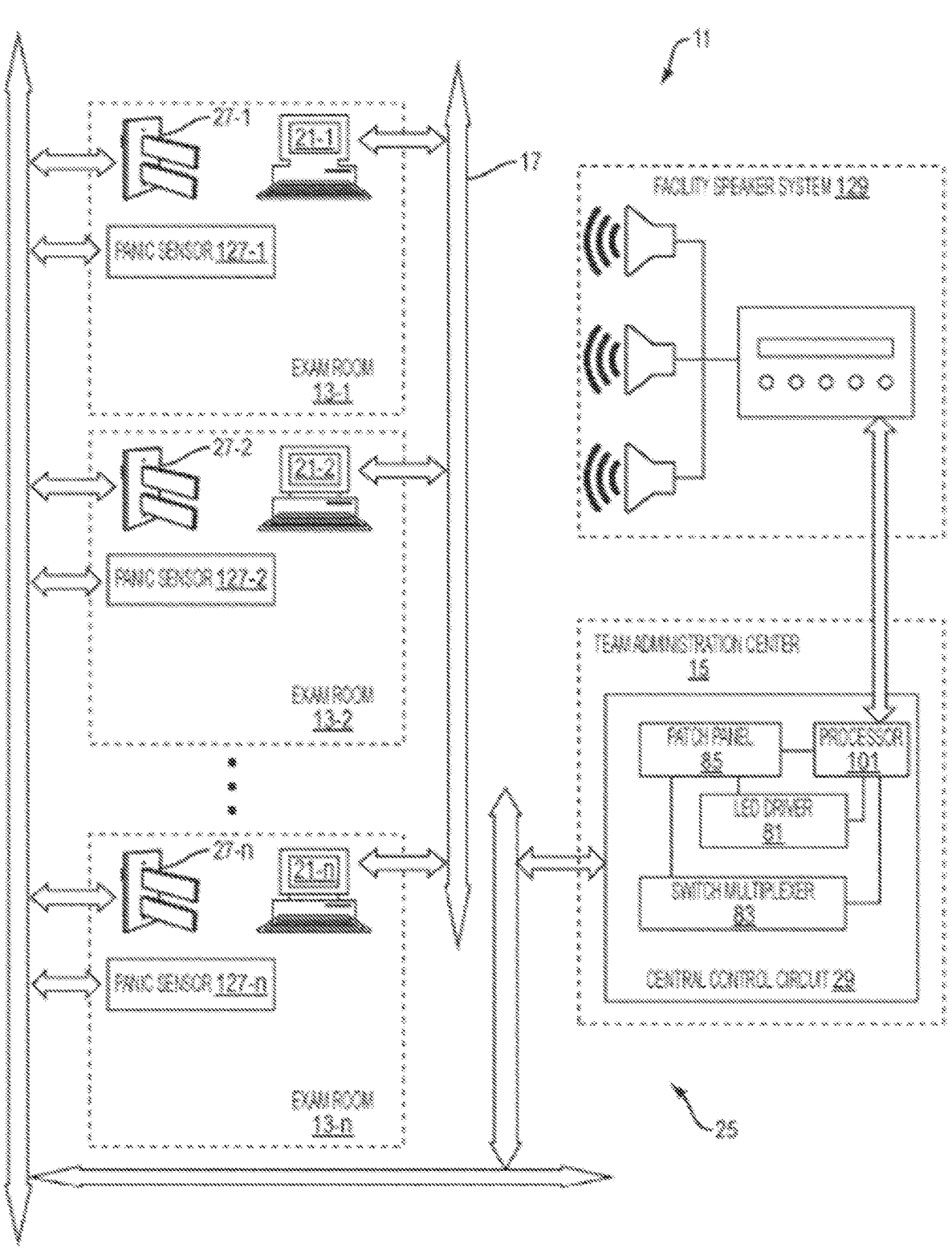
FIG. 17 contains a schematic representation of a patient treatment status notification system in another healthcare facility, according to certain embodiments of the disclosed subject matter herein.

Referring now to FIG. 17, for example, the eFLAG system can be modified to provide the healthcare facility 11 with a way for initiating an auditory emergency alert condition through a designated unit or throughout a larger section of the healthcare facility 11. In some embodiments, the eFLAG system 25 can include a panic broadcast subsystem that can include a set of panic sensors 127-1 thru 127-n, with a panic sensor 127 located inside each examination room 13. Each panic sensor 127 can be in the form of a momentary pushbutton switch (e.g., of the same type as the control device 31) that is, in turn, electrically coupled to the central control circuit 29.

In operation, when a panic sensor 127 in a specific examination room 13 is manually activated (e.g., when the occupant of the examination room 13 depresses the momentary pushbutton switch during an emergency), the eFLAG system 25 can broadcast an alert signifying the emergency status. In some embodiments, the eFLAG system 25 can generate an audio signal containing a description and location of the emergency (e.g., "Code Blue! Code Blue! Code Blue in Internal Medicine Exam Room 13-2"). This audio signal can be conveyed via the central control circuit 29 to a facility speaker subsystem 129 in connection therewith. In response, the facility speaker subsystem 129 can broadcast an audible alert signal to a selection of speakers installed within the healthcare facility 11. Additionally, the eFLAG system 25 can activate the lights for the visual status indicator 27 for the specific examination room 13 that triggered the emergency status. In some embodiments, the eFLAG system 25 can generate a flashing light pattern that is unique to the triggered emergency (e.g., alternately blinking the colors (e.g., red and blue) of the top blade 57-1 and the bottom blade 57-2). This unique visual characteristic can immediately provide to first responders a visual clue that is helpful in identifying the specific room with the emergency.

Figure 18:
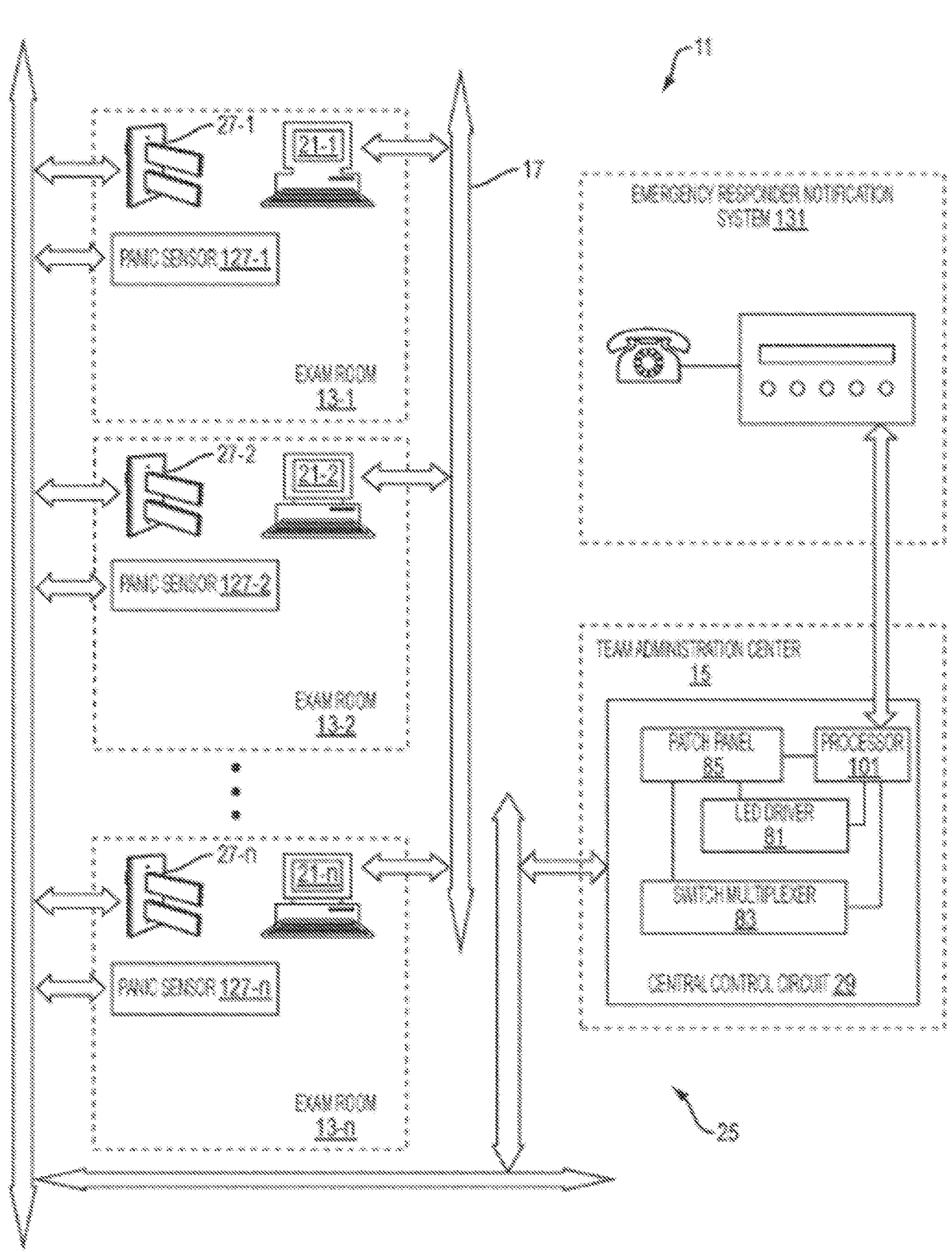
FIG. 18 contains a schematic representation of a patient treatment status notification system in another healthcare facility, according to certain embodiments of the disclosed subject matter herein.

Referring now to FIG. 18, for example, the eFLAG system could be modified to generate a silent alarm. In some embodiments, the eFLAG system 25 can provide the health-care facility 11 with a way for initiating a more discreet emergency alert condition. For example, the eFLAG system 25 can include a discreet panic alert subsystem that includes a set of panic sensors 127-1 thru 127-n, with a panic sensor located in each examination room 13 in communication with the central control circuit 29.

The discreet alert subsystem can differ from the panic broadcast subsystem illustrated in FIG. 17 in that, when a panic sensor 127 in a specific examination room 13 is activated (e.g., when the occupant of the examination room 13 depresses a momentary pushbutton switch during an emergency), the eFLAG system 25 can generate a relatively unobtrusive alert signal. In some embodiments, the eFlag system 25 can transmit a corresponding signal to an emergency responder notification subsystem 131. In response, the subsystem 131 may send an automated voice message to designated telephones or alert a dispatcher to manually call designated telephones, as well as activate the lights for the visual status indicator 27 for the specific examination room 13 that has an emergency status, generating a flashing light pattern unique to the emergency (e.g., alternately blinking the colors (e.g., red and blue) of the top blade 57-1 and the bottom blade 57-2). Additionally, the eFLAG system 25 may activate the lights within the visual status indicator 27 associated with other examination rooms 13 in order to provide an intuitive visual clue that can direct the first responders to the particular room having the emergency (e.g., all bottom blades 57-2 of the visual status indicator 27 could illuminate in a sequential pattern in the hallways leading up to the examination room with the emergency, while still indicating the status of rooms that still have patients within them). In some embodiments, the eFLAG system 25 can combine functionality shown in FIG. 17 with functionality shown in FIG. 18, such that both a speaker system announcement as well as a silent emergency response notification could occur simultaneously.

In some situations, during certain times of the day or certain days of the week patients may be in the building with only lesser-trained staff (e.g., phlebotomists) who are not qualified to respond to medical emergencies. The eFLAG system 25 can be configured such that based on the time of day and day of week, the overhead paging system announcement can be modified to announce that an ambulance has been called. In addition, the eFLAG system 25 can be interfaced to a security alarm system and trigger a zone on the alarm. The alarm monitoring company would be notified in advance that when this particular zone's alarm is triggered, they should call for an ambulance to come to this department.

IX. Additional Embodiments

While a visual status indicator outside an examination room can convey the status of that room, for a larger healthcare facility it may be difficult to view several hallways simultaneously to, for instance, identify which rooms need cleaning or are available for the next patients. In some embodiments, referring back to FIG. 1, an eFLAG system 25 can also include a central display module (e.g., TeamBoard 85) to assemble and display the status of multiple or all examination rooms in a healthcare facility.

In some embodiments, a TeamBoard 85 can include computer software program for communication with an EHR system and the rest of the eFLAG system 25, and a computer monitor for displaying the information. In operation, TeamBoard can send a request to the EHR system for the status of certain examination room(s). In response, the EHR system can be configured or modified to recognize such a request and return the status of each examination room requested including, for example, how long the room has been in that status, and information that had been previously conveyed by the eFLAG system to the EHR system. If the healthcare provider is in the examination room, the EHR system can also look into its schedule to see how long that patient's visit was supposed to be for and send that information as well back to TeamBoard. The Team-Board can then display all of the examination rooms and their statuses and, optionally, highlight any examination rooms that have been in that status an excessively long period of time (e.g., patient waiting for a physician, or a physician with the patient longer than was scheduled).

The TeamBoard can also display the patient wait time for each healthcare provider, so that the healthcare providers and staff know how late they are running. This information can be calculated using a software enhancement to the EHR system and then conveyed to the TeamBoard for display. The TeamBoard can also allow other display screens to be made visible for a period of time (fixed or variable), such as a display screen showing telephone statistics from a separate application. The TeamBoard can also be synchronized so that if multiple TeamBoards are in use, one can display the eFLAG system status and wait times while the other shows telephone statistics, and then each can switch simultaneously to show the alternate screen. The multiple display arrangement can be configurable, e.g., switching the two display screens.

The TeamBoard can be highly configurable, including but not limited to showing any floorplan, colors for statuses, whether or not to allow other screens to be seen, and how frequently to switch to alternative screens. In one example, the TeamBoard can use any JPEG or PNG image file as the background so that it can accommodate as simple or complex a floorplan as desired. Optionally, a "You are here" icon can be placed on top of the floorplan image so that a user can orient his/her perspective as he/she looks at the floorplan. In another example, other statuses of the examination rooms (e.g., a provider waiting for a nurse to come to a room, or a Code Blue in the room) can be visualized on the TeamBoard.

In some embodiments, integration of the eFLAG system 25 with an EHR system, via the EHR controller 23, can allow the eFLAG system 25 to send push notifications to the proper personnel through the EHR system. In some embodiments, an EHR system can have built-in functionality that allows secure messages to be sent to users or groups of users, e.g., to their mobile devices. The EHR system can also have the ability to alert the user with a "Push Notification" that they just received a new secure message. In one example, the eFLAG system 25 can trigger a "Push Notification," which can be visible on a locked smartphone, whereas the user would have to login to an application on the phone to see the associated secure message. In another example, the eFLAG system 25 can trigger a "Push Notification," with all of the information that the user needs to know without having to login to the phone or an application on the phone. These Push Notifications can be configured to be sent only to the people who need to know them, and only at the time that they are relevant and actionable.

The eFLAG system 25 can trigger Push Notifications via the EHR system in multiple situations. For example, when a healthcare provider (e.g., physician) is done seeing the patient and needs another staff member to come to room to perform a task, the healthcare provider can press or turn the control device 31 (e.g., a rotary pushbutton) upon exiting the room to set a new status that requests another particular type of staff member. As a result, the eFLAG system 25 can change the visual status indicator in the examination room to convey that type of staff member requested and can also alert, via a Push Notification of the EHR system, which staff member is being requested. In some embodiments, the Push Notification can be configured to alert one or more staff members of the type desired, show the number of the room that is ready for them, identify the healthcare provider who requested them, and any orders that the healthcare provider may have placed in the EHR system that need to be done by the staff member (e.g., giving a treatment such as a breathing treatment, or doing a procedure such as cleaning out ear wax or putting a dressing on a wound, or doing a test such as doing a throat culture). In some embodiments, healthcare providers (e.g., medical staff) can use standard functionality in the EHR system to assign themselves to groups that will receive the message (e.g., Internal Medicine MA Pager Pool or Pediatric Nurse Pager Pool). In this example, healthcare providers (e.g., medical staff) can respond in a timely manner without having to keep checking for status changes of the examination rooms, e.g., by looking up at the visual status indicators outside each examination room or viewing the TeamBoard.

When a patient arrives at the healthcare facility 11 to check in, the patient usually identifies him/herself and identifies the nature of the visit. The check-in process is usually either initiated by (i) the patient (e.g., using a compatible software application, such as the MyChart mobile application or the Welcome application running on a kiosk) or (ii) an office administrator present at the healthcare facility 11.

In some embodiments, if self-registration is undertaken by the patient via a check-in kiosk (e.g., in a facility lobby), a camera equipped in the kiosk can automatically capture a digital photograph of the patient and load the image linked to the patient chart in the medical health records software. If an office administrator present at the healthcare facility 11 manually performs the check-in registration process, a camera located in the vicinity of the office administrator, which can be incorporated into the wall or another useful object such as a clock, can automatically capture a digital photograph of the patient and load the image linked to the patient chart in the medical health records software. Both of these methods of photography can be automatically triggered by a system integrating with the medical health records software with additional software which identifies when a patient is checking in and which camera to use to take their photo. In this manner, a medical assistant can readily identify the patient in the waiting room and personally greet them in a manner more effectively respecting the patient's privacy (e.g., by eliminating the need to call the name of the patient in a crowded waiting room), thereby creating a more comforting, friendly, and quiet waiting room atmosphere. Optionally, the photo of the patient can be displayed in the schedule in the EHR system and/or on the TeamBoard. In some embodiments, upon completion of the patient examination process, the captured image can be automatically or manually erased from the patient health record for privacy and security purposes.

In this example, the healthcare facility 11 can be designed to discreetly capture a photograph of a patient at initial check-in, either manually or automatically. By capturing a photo and, in turn, linking the photo with the patient file, a medical assistant is able readily identify and personally greet the patient in the waiting room.

In other embodiments, if self-registration is undertaken by the patient via a check-in kiosk (e.g., in a facility lobby), an electronic relay switch attached to the kiosk can be automatically triggered by a system integrating with the medical health records software with additional software which identifies when a patient is checking in at that kiosk, and when the check-in process is complete. This relay switch can activate a kiosk screen sterilization method after the completion of the check-in process at the kiosk. In other embodiments, this electronic relay switch attached to the kiosk can be automatically triggered by a time-of-flight sensor to detect the presence of a patient using the kiosk, and determine with that patient has left so that the relay switch can activate a kiosk screen sterilization method.

When a patient is waiting in an examination room for a healthcare provider, it is an opportunity to entertain and educate the patient so that he/she doesn't feel like he/she is wasting time. In some embodiments, while the patient awaits examination by the designated physician, a customized screen saver (RoomEd) can be activated on one or more monitors in the examination room 13. The screen saver can be customized for the patient based on the designated provider and data associated with the patient in the EHR system. For instance, if the patient suffers from a notable medical condition, information slides relating to the condition may be displayed to the patient for educational purposes. Optionally, through a prior setup process, a defined set of screen saver slides which are chosen by the designated physician (e.g., displaying notable information about the physician or related to the physician's specialty, facility or organization) may also display on linked monitors for viewing. In this manner, the patient remains engaged and relaxed while waiting for the attending physician.

In some embodiments, the RoomEd screensaver software computer can communicate with the EHR system each morning to determine which images it will likely need to display during that day. The EHR system can check which healthcare providers are scheduled to see patients that day and determine which provider-specific, department-specific, specialty-specific, and/or patient-specific images that the RoomEd screensaver should display that day. The RoomEd screensaver can then download those images in advance or on demand if the local computer does not already have the right images or the latest version thereof. When the RoomEd screensaver is activated (for example, when a staff presses a key-combination, e.g., Windows-Z, on the local computer in the examination room), the RoomEd screensaver software can communicate with the EHR system to find out which images to display, e.g., based on the patient and provider that are in that examination room or the schedule. The RoomEd screensaver software can display those images as a slideshow to the patient until there is movement of the mouse or keyboard. In this example, the RoomEd screensaver software via integration with the EHR system can determine and display educational and entertaining images based on the providers, their department, their specialty, the organization, and the specific problems that the patient has.

The invention claimed is:
1. A system, comprising:
an electronic health record (EHR) controller configured to store data identifying a patient and data identifying a healthcare provider for the patient and to receive data identifying a first status selected from a plurality of statuses associated with a treatment cycle identified for the patient, wherein the treatment cycle identifies an occurrence order of the plurality of statuses;

a visual status indicator comprising:

a first light configured to indicate the first status of the plurality of statuses associated with the treatment cycle identified for the patient by emitting first colored light for the first status selected from a plurality of colors of light for the plurality of statuses based at least in part on the data received at the EHR controller that identifies the first status for the patient; and a second light configured to indicate the healthcare provider identified for the patient within the data stored by the EHR controller by emitting second colored light for the healthcare provider selected from a plurality of colors of light, wherein data identifying the healthcare provider is determined based at least in part on data identifying the patient is in an examination room, wherein the first light is adjustable among the plurality of colors of light for the plurality of statuses independently of the second colored light;

an occupancy detection sensor configured to generate an occupancy detection signal identifying whether the patient is in the examination room;

a control device in communication with the visual status indicator and the EHR controller, the control device configured to control the first light and the second light based at least in part on data stored at the EHR controller;

wherein the patient is assigned to the examination room within health records for the patient stored in the EHR controller; and a central control circuit coupled with the visual status indicator, the control device, the occupancy detection sensor, and the EHR controller, wherein the central control circuit is configured to:

cause the first light to emit a first colored light in a first color identifying the first status and a current treatment status of the patient as indicated in the health records of the patient, cause the first light to change the first colored light to identify a second status based at least in part on the occurrence order of the plurality of statuses associated with the treatment cycle and one or more of (i) a first signal input by a user that is received from the control device or (ii) information received from the EHR controller, and cause the first light to change the first colored light to identify a third status based at least in part of the occurrence order of the plurality of statuses associated with the treatment cycle and on the occupancy detection signal received from the occupancy detection sensor.

2. The system of claim 1, wherein the EHR controller is further configured to:

determine a visit time for a healthcare provider based at least in part on receiving the data identifying the first status selected from the plurality of statuses and at least one of: (i) the first signal input by the user or (ii) the information from the EHR controller.

3. The system of claim 1, wherein the EHR controller is further configured to:

determine one or more anticipated wait times for one or more patients based at least in part on receiving the data identifying the first status selected from the plurality of statuses.

4. The system of claim 1, further comprising:

a computing device in communication with the central control circuit, wherein the central control circuit is further configured to cause the second light to change the second colored light based at least in part on the user logging into the computing device.

5. The system of claim 1, further comprising:

a computing device in communication with the central control circuit, wherein the central control circuit is further configured to cause the first light to change the first colored light based at least in part on the user inputting a command at the computing device.

6. The system of claim 1, wherein the second light is further configured to alternate between emitting the second colored light and a third colored light for indicating a second healthcare provider.

7. The system of claim 1, wherein causing the first light to emit the first colored light in the first color identifying the first status comprises solidly illuminating the first colored light in the first color;

the central control circuit is further configured to cause the first light to blink in the first colored light at a first rate if the first status is indicated by the first light for at least a waiting time threshold; and wherein causing the first light to change the first colored light to identify a second status comprises solidly illuminating the first light to identify the second status.

8. The system of claim 7, wherein the central control circuit is further configured to cause the first light to blink at a second rate after a second threshold time after the EHR controller receives the data identifying the first status.

9. The system of claim 1, further comprising:

a door sensor configured to detect opening and closing of a door of an examination room, wherein:

the central control circuit is further configured to cause one or more of the first light to change the first colored light or the second light to change the second colored light based at least in part on a door detection signal from the door sensor.

10. The system of claim 1, wherein:

health records stored by the EHR controller comprise data indicating treatment start time, treatment duration, and patient wait time.

11. The system of claim 1, wherein:

the central control circuit is configured to trigger a push notification at a device of the user in response to causing the first light to change the first colored light.

12. The system of claim 1, wherein:

the EHR controller is configured to store wait time data; and the central control circuit is configured to compare wait time data against a waiting time threshold.

13. The system of claim 1, wherein:

the control device comprises a rotary pushbutton configured for receiving a press action and at least one of a clockwise rotation action or a counterclockwise rotation action from the user.

14. The system of claim 1, further comprising:

a medical emergency input device, wherein the medical emergency input device is configured to generate a medical emergency signal when activated by the user.

15. The system of claim 14, wherein:

the central control circuit is further configured to change a color and blink rate of at least one of the first light and the second light in response to receiving the medical emergency signal.

16. The system of claim 1, wherein:

the EHR controller comprises a network server.

17. The system of claim 1, further comprising:

a central display system in communication with the EHR controller and configured to display the first status of the plurality of statuses and the healthcare provider.

18. The system of claim 1, wherein the central control circuit is further configured to:

when causing the first light to change the first colored light to identify a third status based at least in part of the occurrence order of the plurality of statuses associated with the treatment cycle and on the occupancy detection signal received from the occupancy detection sensor, further turning off the second light while the first light identifies the third status.

\* \* \* \* \*